United States Patent
Brown et al.

(12)

(10) Patent No.: US 6,509,447 B1
(45) Date of Patent: Jan. 21, 2003

(54) G PROTEIN CHIMERAS AND METHODS OF SCREENING COMPOUNDS

(75) Inventors: Andrew James Brown, Hitchin (GB); Simon Jeremy Dowell, St. Albans (GB)

(73) Assignee: Glaxo Welcome Inc., Middlesex (GB)

( * ) Notice: Subject to any disclaimer, the term of this patent is extended or adjusted under 35 U.S.C. 154(b) by 0 days.

(21) Appl. No.: 09/508,429

(22) PCT Filed: Sep. 11, 1998

(86) PCT No.: PCT/GB98/02759

§ 371 (c)(1),
(2), (4) Date: May 26, 2000

(87) PCT Pub. No.: WO99/14344

PCT Pub. Date: Mar. 25, 1999

(30) Foreign Application Priority Data

Sep. 13, 1997 (GB) .............................. 9719496

(51) Int. Cl.⁷ ........................ C12P 21/08; C12P 21/06; C12P 21/04; C12N 1/14; C07H 21/02

(52) U.S. Cl. ................. 530/387.3; 435/69.9; 435/70.1; 435/71.1; 435/471; 435/69.1; 435/7.2; 435/254.2; 536/23.1; 536/23.5

(58) Field of Search ...................... 530/387.3; 435/7.1, 435/7.2, 69.1, 70.1, 71.1, 255.1, 254.2, 471, 69.9; 536/23.5, 23.1

(56) References Cited

FOREIGN PATENT DOCUMENTS

| WO | WO 98 16557 | 4/1989 |
|----|-------------|--------|
| WO | WO 95 21925 | 8/1995 |

OTHER PUBLICATIONS

Kallal and Kurjan. Mol. Cell. Biol. 17:2897–2907, 1997.*
Kang et al. Mol. Cell Biol. 10:2582–2590, 1990.*
Conklin et al, "Carboxyl–terminal mutations of Gq alpha and Gs alpha that alter the fidelity of receptor activation" *Molecular Pharmacology*, vol. 50, No. 4, Oct. 1996, pp. 885–890.

* cited by examiner

*Primary Examiner*—Gary L. Kunz
*Assistant Examiner*—Robert S. Landsman
(74) *Attorney, Agent, or Firm*—Nixon & Vanderhye, P.C.

(57) ABSTRACT

A chimeric $G_\alpha$ protein having yeast $G_\alpha$ (Gpa1p) amino acid sequences modified by a minimum of 3 amino acids positions within the C-terminal 10 amino acids by substitution by alternative amino acids, a transformed yeast cell comprising said chimeric $G_\alpha$ protein and a method of screening for a compound able to interact with a receptor comprising contacting a compound of interest with said yeast cell and observing the growth response of the cell or observing production of a reporter gene product.

7 Claims, 23 Drawing Sheets

SEQUENCE LISTING

<160> NUMBER OF SEQ ID NOS: 22

<210> SEQ ID NO 1
<211> LENGTH: 29
<212> TYPE: DNA
<213> ORGANISM: Artificial Sequence
<220> FEATURE:
<223> OTHER INFORMATION: Description of Artificial Sequence:
      Oligodeoxynucleotide

<400> SEQUENCE: 1
ttaaggaata caacctagtt tgaattccg                                    29

<210> SEQ ID NO 2
<211> LENGTH: 29
<212> TYPE: DNA
<213> ORGANISM: Artificial Sequence
<220> FEATURE:
<223> OTHER INFORMATION: Description of Artificial Sequence:
      Oligodeoxynucleotide

<400> SEQUENCE: 2
tcgacggaat tcaaactagg ttgtattcc                                    29

<210> SEQ ID NO 3
<211> LENGTH: 29
<212> TYPE: DNA
<213> ORGANISM: Artificial Sequence
<220> FEATURE:
<223> OTHER INFORMATION: Description of Artificial Sequence:
      Oligodeoxynucleotide

<400> SEQUENCE: 3
ttaagcaata cgaactattg tgaattccg                                    29

<210> SEQ ID NO 4
<211> LENGTH: 29
<212> TYPE: DNA
<213> ORGANISM: Artificial Sequence
<220> FEATURE:
<223> OTHER INFORMATION: Description of Artificial Sequence:
      Oligodeoxynucleotide

<400> SEQUENCE: 4
tcgacggaat tcacaatagt tcgtattgc                                    29

<210> SEQ ID NO 5
<211> LENGTH: 29
<212> TYPE: DNA
<213> ORGANISM: Artificial Sequence
<220> FEATURE:
<223> OTHER INFORMATION: Description of Artificial Sequence:

Oligodeoxynucleotide

<400> SEQUENCE: 5
ttaagggttg tggcttgtac tgaattccg					29

<210> SEQ ID NO 6
<211> LENGTH: 29
<212> TYPE: DNA
<213> ORGANISM: Artificial Sequence
<220> FEATURE:
<223> OTHER INFORMATION: Description of Artificial Sequence:
      Oligodeoxynucleotide

<400> SEQUENCE: 6
tcgacggaat tcagtacaag ccacaaccc					29

<210> SEQ ID NO 7
<211> LENGTH: 29
<212> TYPE: DNA
<213> ORGANISM: Artificial Sequence
<220> FEATURE:
<223> OTHER INFORMATION: Description of Artificial Sequence:
      Oligodeoxynucleotide

<400> SEQUENCE: 7
ttaaggattg tggtttgttt tgaattccg					29

<210> SEQ ID NO 8
<211> LENGTH: 29
<212> TYPE: DNA
<213> ORGANISM: Artificial Sequence
<220> FEATURE:
<223> OTHER INFORMATION: Description of Artificial Sequence:
      Oligodeoxynucleotide

<400> SEQUENCE: 8
tcgacggaat tcaaaacaaa ccacaatcc					29

<210> SEQ ID NO 9
<211> LENGTH: 28
<212> TYPE: DNA
<213> ORGANISM: Artificial Sequence
<220> FEATURE:
<223> OTHER INFORMATION: Description of Artificial Sequence:
      Oligodeoxynucleotide

<400> SEQUENCE: 9
ttaaggatgt ggtttgtact gaattccg					28

<210> SEQ ID NO 10
<211> LENGTH: 29
<212> TYPE: DNA
<213> ORGANISM: Artificial Sequence
<220> FEATURE:
<223> OTHER INFORMATION: Description of Artificial Sequence:
      Oligodeoxynucleotide

<400> SEQUENCE: 10
tcgacggaat tcagtacaaa ccacattcc					29

<210> SEQ ID NO 11
<211> LENGTH: 29
<212> TYPE: DNA
<213> ORGANISM: Artificial Sequence
<220> FEATURE:
<223> OTHER INFORMATION: Description of Artificial Sequence:
      Oligodeoxynucleotide

<400> SEQUENCE: 11
ttaagtatat aggcttgtgt tgaattccg                              29

<210> SEQ ID NO 12
<211> LENGTH: 29
<212> TYPE: DNA
<213> ORGANISM: Artificial Sequence
<220> FEATURE:
<223> OTHER INFORMATION: Description of Artificial Sequence:
      Oligodeoxynucleotide

<400> SEQUENCE: 12
tcgacggaat tcaacacaag cctatatac                              29

<210> SEQ ID NO 13
<211> LENGTH: 29
<212> TYPE: DNA
<213> ORGANISM: Artificial Sequence
<220> FEATURE:
<223> OTHER INFORMATION: Description of Artificial Sequence:
      Oligodeoxynucleotide

<400> SEQUENCE: 13
ttaaggatat tatgttgcaa tgaattccg                              29

<210> SEQ ID NO 14
<211> LENGTH: 29
<212> TYPE: DNA
<213> ORGANISM: Artificial Sequence
<220> FEATURE:
<223> OTHER INFORMATION: Description of Artificial Sequence:
      Oligodeoxynucleotide

<400> SEQUENCE: 14
tcgacggaat tcattgcaac ataatatcc                              29

<210> SEQ ID NO 15
<211> LENGTH: 29
<212> TYPE: DNA
<213> ORGANISM: Artificial Sequence
<220> FEATURE:
<223> OTHER INFORMATION: Description of Artificial Sequence:
      Oligodeoxynucleotide

<400> SEQUENCE: 15
ttaagcaatt gatgctacag tgaattccg                              29

<210> SEQ ID NO 16
<211> LENGTH: 29
<212> TYPE: DNA
<213> ORGANISM: Artificial Sequence
<220> FEATURE:
<223> OTHER INFORMATION: Description of Artificial Sequence:
      Oligodeoxynucleotide

<400> SEQUENCE: 16
tcgacggaat tcactgtagc atcaattgc                              29

<210> SEQ ID NO 17
<211> LENGTH: 29
<212> TYPE: DNA
<213> ORGANISM: Artificial Sequence
<220> FEATURE:
<223> OTHER INFORMATION: Description of Artificial Sequence:
      Oligodeoxynucleotide -continued

```
<400> SEQUENCE: 17
ttaaggaatt taacttggtt tgaattccg                                      29

<210> SEQ ID NO 18
<211> LENGTH: 29
<212> TYPE: DNA
<213> ORGANISM: Artificial Sequence
<220> FEATURE:
<223> OTHER INFORMATION: Description of Artificial Sequence:
      Oligodeoxynucleotide

<400> SEQUENCE: 18
tcgacggaat tcaaaccaag ttaaattcc                                      29

<210> SEQ ID NO 19
<211> LENGTH: 29
<212> TYPE: DNA
<213> ORGANISM: Artificial Sequence
<220> FEATURE:
<223> OTHER INFORMATION: Description of Artificial Sequence:
      Oligodeoxynucleotide

<400> SEQUENCE: 19
ttaaggaaat taacctattg tgaattccg                                      29

<210> SEQ ID NO 20
<211> LENGTH: 29
<212> TYPE: DNA
<213> ORGANISM: Artificial Sequence
<220> FEATURE:
<223> OTHER INFORMATION: Description of Artificial Sequence:
      Oligodeoxynucleotide

<400> SEQUENCE: 20
tcgacggaat tcacaatagg ttaatttcc                                      29

<210> SEQ ID NO 21
<211> LENGTH: 24
<212> TYPE: DNA
<213> ORGANISM: Artificial Sequence
<220> FEATURE:
<223> OTHER INFORMATION: Description of Artificial Sequence:
      Oligodeoxynucleotide

<400> SEQUENCE: 21
ttaagtgagc ggccgcgaat tccg                                           24

<210> SEQ ID NO 22
<211> LENGTH: 24
<212> TYPE: DNA
<213> ORGANISM: Artificial Sequence
<220> FEATURE:
<223> OTHER INFORMATION: Description of Artificial Sequence:
      Oligodeoxynucleotide

<400> SEQUENCE: 22
tcgacggaat tcgcggccgc tcac                                           24
```

G PROTEIN CHIMERAS AND METHODS OF SCREENING COMPOUNDS

The present application is a 371 of PCT/GB98/02759, filed Sep. 11, 1998.

The present invention relates to chimeric G proteins, expression constructs therefor, yeast cells expressing such constructs and methods of making and using them.

G protein-coupled receptors are integral membrane proteins, characteristically with 7 transmembrane domains, which convey hormonal and sensory signals to the cell interior (see (1) for review). These receptors are commonly referred to as 7TM receptors or 7TMRs. The receptors respond to ligand binding by activating heterotrimeric G proteins composed of α, β and γ subunits. The $G_\alpha$ subunit is bound to GDP in the G protein trimer, and interaction with an activated (ligand bound) receptor induces the replacement of GDP with GTP. Accompanying conformational changes result in the dissociation of $G_\alpha$-GTP and the $G_\beta/G_\gamma$ particle, either of which can modulate ion channel or enzyme effectors to cause signal propagation. The signal persists until $G_\alpha$, which has GTPase activity, hydrolyses the bound GTP, allowing reassembly of the heterotrimer. Members of the RGS (Regulator of G protein Signalling) protein family regulate signal duration by acting as GAPs (GTPase activating proteins) for the $G_\alpha$ subunit (38) (17). The G protein signalling system appears to be common to all eukaryotes.

A well-characterised example of the trimeric G protein signalling system is the pheromone response pathway of the budding yeast Saccharomyces cerevisiae (20). Cells of the MATa mating type express a receptor encoded by the STE2 gene. This receptor becomes activated upon binding of the α-factor mating pheromone, a peptide secreted by cells of the opposite (MATα) mating type. The yeast G protein is assembled from the products of the GPA1 ($G_\alpha$), STE4 ($G_\beta$), and STE18 ($G_\gamma$) genes. The $G_\beta/G_\gamma$ (Ste4p/Ste18p) particle released upon activation of the Ste2p receptor conveys the signal to a mitogen-activated protein kinase (MAPK) module. This leads to activation of the cyclin-dependent kinase inhibitor Far1p, causing cell cycle arrest and transcriptional induction of a set of genes involved in the mating process, including FUS1. The pathway is desensitised by Sst2p, a member of the RGS family. Cells of the opposite mating type (MATα) express a different receptor (Ste3p) and thereby respond to the pheromone (a-factor) secreted by MATa cells; otherwise the signalling apparatus utilised in the two mating types is the same.

At present, at least 16 $G_\alpha$ subunits, 5 $G_\beta$ subunits and 11 $G_\gamma$ subunits have been identified in mammals, which can assemble a wide diversity of trimeric G proteins. On the basis of sequence homology, the $G_\alpha$ subunits fall into at least four families, related to $G_{\alpha i}$, $G_{\alpha s}$, $G_{\alpha q}$, or $G_{\alpha 12}$. Typically, a given 7TM receptor activates only a single or small subset of $G_\alpha$ subunits. Thus even in cells which express multiple $G_\alpha$ subunits, signalling may be specific to particular G proteins and their downstream signalling pathways. A combination of approaches has defined several specific regions of the $G_\alpha$ subunit as key determinants of receptor/G protein specificity. These include regions in the N-terminus, the switch II to switch III regions (21) which are primarily responsible for binding $G_\beta/G_\gamma$, and particularly regions of the C-terminus. For example, a cluster of mutations occurring in the C-terminal region of $G_\alpha$ have been found to cause defects in receptor coupling ((29)(13) and references therein). Also, peptides modelled on the C-termini of $G_{\alpha t}$ (transducin) and $G_{\alpha i2}$ compete for binding to rhodopsin and the β-adrenergic receptor, respectively (9)(30)(35) and antibodies directed against the $G_\alpha$ C-terminus can also block interaction with receptors (6)(10)(36). The normal response to agonist stimulation of the adenosine $A_1$ receptor in cultured mammalian cells (e.g. COS cells) is the activation of $G_{\alpha i}$-family proteins, resulting in inhibition of adenylate cyclase. $G_{\alpha q}$-containing heterotrimers in contrast do not normally respond to $A_1$ activation. However, $G_{\alpha q}$ subunit can be induced to interact with the $A_1$ receptor by exchanging the C-terminal four amino acids of $G_{\alpha q}$ for the corresponding amino acids of $G_{\alpha i2}$ (7). Hence, phospholipase C (an effector of activated $G_{\alpha q}$) can be activated by adenosine A1 receptor agonists when signalling is mediated by a chimeric $G_\alpha$ subunit (7). The somatostatin $SST_3$ receptor is incompatible with $G_{\alpha s}$, but can be coupled to the activation of adenylate cyclase in COS cells by replacement of five C-terminal amino acids of $G_{\alpha s}$ with corresponding residues from either $G_{\alpha i2}$, which is known to interact with the $SST_3$ receptor, or from $G_{\alpha 16}$(18). $G_{\alpha 15}$ and $G_{\alpha 16}$ interact with a wide range of 7TM receptors (26), and are unusual in this respect. In crystal structures which have been solved for $G_{i1}$ (41) and $G_t$ (19) trimers, the $G_\alpha$ C-terminal tail lies on a flat, largely uncharged surface of the G protein trimer which also includes two lipid groups covalently attached to the $G_\alpha$ N-terminus and the $G_\gamma$ C-terminus. This surface is believed to face the membrane and to be involved in interactions with the intracellular loops of the 7TM receptor.

Several reports have demonstrated that the yeast G protein signalling system can be coupled to heterologously expressed mammalian G protein-coupled (7TM) receptors. Some receptors, including the rat somatostatin $SST_2$ receptor (33), and the rat adenosine $A_{2a}$ receptor (34), can interact directly with the yeast $G_\alpha$ protein Gpa1p, whereas other receptors, including the human growth hormone releasing hormone receptor (GHRHR)(12), are incompatible with Gpa1p. In order to allow coupling of these receptors, the yeast $G_\alpha$ subunit can be deleted and the heterologous receptor co-expressed with a full-length mammalian $G_\alpha$ subunit. Alternatively, chimeric $G_\alpha$ subunits have been used in which the C-terminal domain (approx. one third of the peptide sequence) of Gpa1p is replaced with the equivalent region of a mammalian $G_\alpha$ subunit. See WO95/21925 (American Cyanamid Company) for both approaches. Chimeras, or other modified or heterologous $G_\alpha$ subunits must satisfy several criteria to be useful in a yeast coupling system. Most importantly, they must bind efficiently to yeast $G_\beta/G_\gamma$ to prevent signalling in the absence of activated 7TM receptor, and they must effectively interact with agonist-bound activated receptors to be capable of signal propagation.

Such heterologous or chimeric $G_\alpha$ components can facilitate the coupling of a heterologous 7TM receptor to the yeast signalling system (the pheromone response pathway) so that the effects of ligands such as potential new drug molecules on the receptor can be observed in phenotypic responses of the yeast cells. For example, cells may be induced to grow, and/or to convert an indicator dye compound in response to receptor agonists by introducing reporter genes downstream in the signalling pathway. However, chimeric constructs such as those described in WO95/21925 commonly show reduced affinity for the yeast G protein βγ subunit pair and show increased background signalling. Because of the specificity of a given receptor for one or a small number of the known $G_\alpha$ subunits, different $G_\alpha$ constructs have been required to demonstrate functional coupling activity with the majority of receptors tested.

The discovery of new drugs able to act via 7TM receptors requires screens of high efficiency, yet high specificity.

Currently, the yeast coupling system is constrained by receptor/G protein specificity which imposes a requirement for a wide variety of $G_\alpha$ constructs to be tried for each receptor tested for coupling. For receptors which fail to couple, there is uncertainty as to whether failure is due to receptor/G protein incompatibility, or other reasons such as inappropriate receptor conformation, for example. It would be desirable to be able to couple a number of different receptors to the yeast G protein signalling pathway using a single $G_\alpha$ construct. This can be beneficial in the study of orphan receptors, of which nothing is known of receptor/G protein specificity. Alternatively, an array of $G_\alpha$ constructs could be used in the study of orphan receptors.

Surprisingly, we have found that certain chimeric G proteins, which we refer to as G protein "transplants" can be at least ten-fold more efficient than previously known chimeras in coupling mammalian 7TM receptors to the yeast mating pathway.

Accordingly, in a first aspect the present invention provides a chimeric $G_\alpha$ protein having yeast $G_\alpha$ (Gpa1p) amino acid sequences modified by a minimum of 3 amino acids positions within the C-terminal 10 amino acids by substitution with alternative amino acids. Preferably the chimera includes at least 5 such substitutions.

Accordingly, in a second aspect the present invention provides a chimeric $G_\alpha$ protein having yeast $G_\alpha$ (Gpa1p) amino acid sequences modified at a minimum of three amino acid positions within the C-terminal 10 amino acids by substitution with amino acids from a heterologous $G_\alpha$ protein. Preferably the chimera includes at least 5 substitutions. In preferred embodiments of this aspect of the invention, the chimera includes at least 3, desirably at least 5 consecutive amino acids corresponding to an amino acid sequence derived from the C-terminal 10 amino acids of a heterologous $G_\alpha$ protein. For example, the C-terminal 5 amino acids of a mammalian $G_\alpha$ protein, for example $G_{\alpha 16}$, but feasibly any $G_\alpha$, may replace at least the C-terminal 5 amino acids of the endogenous yeast $G_\alpha$ protein to provide a chimera according to the invention. We have designated such chimeras "transplants" or "transplant chimeras".

The chimeric $G_\alpha$ proteins of the present invention are believed to adopt a conformation which is more compatible with signal transduction in yeast (and is presumed to be closer to the native yeast $G_\alpha$ conformation) than that of previously known chimeras in which the C-terminal domain of the yeast protein was exchanged for that of a mammalian $G_\alpha$ protein. Thus the chimeras of the present invention have the advantage of changing receptor specificity and permitting the coupling of diverse receptors to the yeast signalling pathway with only minimal changes to the Gpa1p sequence. As a result of the close similarity to wild-type Gpa1p, these chimeric $G_\alpha$ subunits retain a similar affinity for $G_\beta/G_\gamma$ as Gpa1p, and expression can be directed by the GPA1 promoter to achieve an optimal stoichiometry of $G_\alpha$. Expression from various other promoters is also compatible with receptor coupling.

In a third aspect, the present invention also provides a nucleotide sequence encoding a chimeric $G_\alpha$ protein according to the present invention. Also provided is an expression vector comprising said nucleotide sequence and capable of expressing the nucleotide sequence on transfection into a suitable host cell. The construction of expression vectors including suitable promoters, transcription termination sequences and marker genes will be apparent to a person skilled in the art. The host cell may desirably be a yeast cell of the species *Saccharomyces cerevisiae* and represents a further aspect of the invention.

Accordingly, the invention also provides a transformed yeast cell comprising a nucleotide sequence which encodes a chimeric $G_\alpha$ protein according to the present invention, for example a heterologous G protein-coupled receptor including receptors for which the ligand is unknown, and a nucleotide sequence which encodes a chimeric $G_\alpha$ protein comprising yeast $G_\alpha$ (Gpa1p) amino acid sequences and at least 3 amino acids derived from the amino acid sequence of the C-terminal 10 amino acids of a $G_\alpha$ protein according to the present invention for example a heterologous $G_\alpha$ protein, such as the mammalian, $G_{\alpha 16}$ protein. The heterologous receptor may be a 7TM receptor. Such receptors include those for acetylcholine, adrenaline, noradrenaline, dopamine, histamine, melatonin, serotonin, angiotensin, prostaglandins, cannabinoids, neuropeptide Y, substance P, opioids, glucagon, angiotensin, bradykinin, chemokines, thrombin, glycoprotein hormones, adenosine, nucleotides, and somatostatin.

Transformed yeast cells according to the present invention may also comprise a nucleotide sequence encoding a reporter gene operatively associated with a promoter responsive to the G protein signalling pathway. Such reporter genes may include HIS3 or other auxotrophic markers (such as URA3, LEU2, or TRP1) or genes which confer resistance or sensitivity to drug selections, such as CYH2 or G418$^R$ or other genes such as those encoding intracellular enzymes such as β-galactosidase (LacZ) and luciferase, or green fluorescent protein (GFP), or genes encoding secreted enzymes such as a phosphatase such as PHO5, or a kinase. Desirably, yeast cells may contain combinations of multiple reporter genes, such as FUS1-HIS3 and FUS1-lacZ. In preferred embodiments the transformed yeast cells will also include mutations in at least one of the GPA1, SST2 or STE2 genes. Preferably such mutations will be deletions. Desirably, FAR1 is also deleted when a reporter gene is used to monitor activity in the G protein signalling pathway. This ensures that growth can continue even under conditions which activate the pheromone response pathway. In alternative embodiments of this invention, the FAR1 gene may remain intact so that agonist stimulation causing activation of the signalling pathway may be monitored as resulting in growth arrest.

Preferred yeast strains will have deletions of SST2 and GPA1 (yeast $G_\alpha$)—the former to prevent down-regulation of the signal by Sst2p activation of GTP-ase, the latter to prevent signal quenching, which occurs when $G_\alpha$ is present in stoichiometric excess to $G_\beta/G_\gamma$, due to rapid reassociation of the actively signalling $G_\beta/G_\gamma$ moiety into the inactive heterotrimer.

We have designated the chimera between the N-terminal 467 amino acids of Gpa1p and the 5 C-terminal amino acids of $G_{\alpha 16}$ as the Gpa1-$G_{\alpha 16}$ transplant. Similarly, the chimera containing the C-terminal 5 amino acids of $G_{\alpha q}$ is designated as the Gpa1-$G_{\alpha q}$ transplant, and the chimera containing the C-terminal 5 amino acids of $G_{\alpha s}$ is designated as the Gpa1-$G_{\alpha s}$ transplant. In addition, the following transplants have also been constructed. They are identical to those described above, ie. they comprise the N-terminal 467 amino acids of Gpa1p and the C-terminal 5 amino acids from a $G_\alpha$ protein as follows: Gpa1-$G_{\alpha 12}$, Gpa1-$G_{\alpha 13}$, Gpa1-$G_{\alpha 14}$, Gpa1-$G_{\alpha i1}$, Gpa1-$G_{\alpha i3}$, Gpa1-$G_{\alpha 0}$ and Gpa1-$G_{\alpha z}$.

A further transplant was prepared between the yeast $G_\alpha$, Gpa1p and Gpa3, a $G_\alpha$ subunit from the yeast *Ustilago maydis*. This transplant is designated Gpa1-Gpa3. These transplants illustrate that by changing the 5 C-terminal amino acids of Gpa1p the specificity of the $G_\alpha$ subunit for receptors can be altered. Also the results indicate that the effectiveness of the "transplants" in coupling to foreign receptors in yeast is unexpectedly good compared to chimeric subunits with longer heterologous $G_\alpha$ regions.

In mammalian cells, the purinergic nucleotide $P2Y_2$ receptor is coupled to the activation of phospholipase $C\beta$ (PLC$\beta$) via $G_{\alpha q}$. We have found that the Gpa1-$G_{\alpha q}$ transplant substantially improves the weak response to agonist observed with wild-type Gpa1p. Similarly, coupling of the somatostatin $SST_2$ receptor achieved with the Gpa1-$G_{\alpha 16}$ transplant was enhanced ten-fold compared to either wild-type Gpa1p or the $G_{\alpha i/o}$ family chimeras, which is remarkable considering this receptor interacts with $G_{\alpha i/o}$ proteins in mammalian cells. Also the $5HT_{1A}$ receptor can interact with the Gpa1-$G_{\alpha 16}$ transplant, even though it fails to stimulate wild-type Gpa1p in MMY9 yeast cells. Minimal amino acid substitutions can confer on yeast Gpa1p the properties of a generic G protein ($G_{\alpha 16}$) which was not possible under previously described approaches to chimera construction. Therefore this invention presents for the first time the possibility of a system comprising a single $G_\alpha$ subunit and able to couple a wide variety of 7TM receptors.

Moreover, we have found that the approach of substituting the five C-terminal amino acids of Gpa1p to generate the transplants is widely applicable, in that we have generated transplants of representative members of all four $G_\alpha$ families: $G_{\alpha i}$, $G_{\alpha s}$, $G_{\alpha q}$ and $G_{\alpha 12}$. This was not possible in previously described approaches to chimera construction. Furthermore, all of the transplants can be expressed from the promoter of the GPA1 gene to achieve optimal stoichiometry for efficient coupling. This was not possible in previously described approaches to chimera construction, as some of these chimeras required expression from stronger promoters, as in the case of Gpa1/$G_{\alpha s}$ (ref:12). Lastly, the pheromone response pathway is not activated in cells which express integrated versions of the transplants in the absence of activated receptors. This indicates that manipulations to the C-terminal amino acids do not interfere with the interaction with $G_\beta/G_\gamma$; this was not true with previously described approaches to chimera construction. Together, our data suggest that the approach of creating transplants will be applicable to any newly discovered mammalian $G_\alpha$, or to $G_\alpha$ subunits not described herein ($G_{\alpha t}$ or $G_{\alpha olf}$) or to $G_\alpha$ subunits derived from any other metazoan species.

BRIEF DESCRIPTION OF THE FIGURES

The invention will now be further described, by way of example and illustration and not of limitation, by the following experimental examples with the aid of figures in which.

MATERIALS AND METHODS

Plasmids and Strains

Nucleic acid manipulations were carried out according to standard methods (24).

Receptor Expression Constructs

Figure 6A:
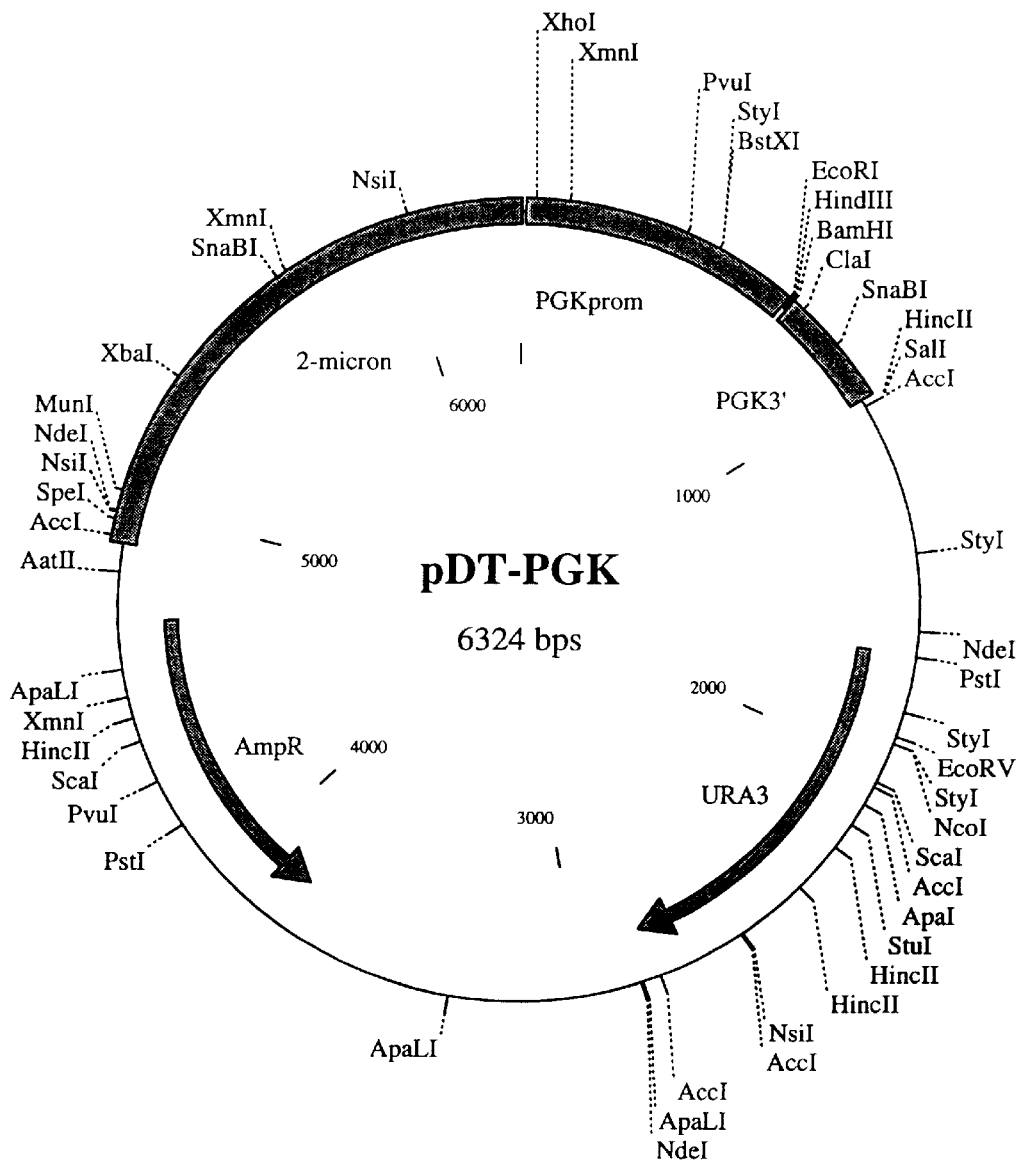
FIGS. 6a–h are diagrammatic representations of certain plasmid constructs used in this study (plasmid maps)

Receptor expression constructs were based on the high copy number episomal yeast-*E.coli* shuttle vectors pFL61 (27), YEp24, and pDT-PGK (see plasmid map of FIG. 6(A)), which is identical to pPGK reported by Kang et al. (14). Complementary DNA (cDNA) sequences encoding unmodified human G protein-coupled receptors were introduced into these vectors between the promoter and terminator regions of the PGK1 gene, to confer strong constitutive expression in yeast cells. The somatostatin $SST_2$ receptor (Genbank accession M81830) was introduced into pFL61. The melatonin $ML_{1B}$ (Genbank accession U25341), somatostatin $SST_5$ (Genbank accession L14865), serotonin $5HT_{1A}$ (Genbank accession X13556), and serotonin $5HT_{1D}$ (Genbank accession M81589) receptors were introduced into pDT-PGK. The purinergic nucleotide P2Y receptor (Genbank accession S81950) and the adenosine $A_{2b}$ receptor (Genbank accession M97759) were also introduced into pDT-PGK. The purinergic nucleotide $P2Y_2$ receptor was also introduced into pDT-PGK. The sequence of the $P2Y_2$ receptor corresponded to that reported by Parr et al. (Genbank accession U07225) (32)(31) except codon 348 was GM (Glu) and not GGA (Gly), potentially as a result of phylogenetic variation. The gene encoding the endogenous yeast α-factor receptor STE2 was expressed from its own promoter using the construct Yep24-STE2.

$G_\alpha$ Expression Constructs

Figure 6B:
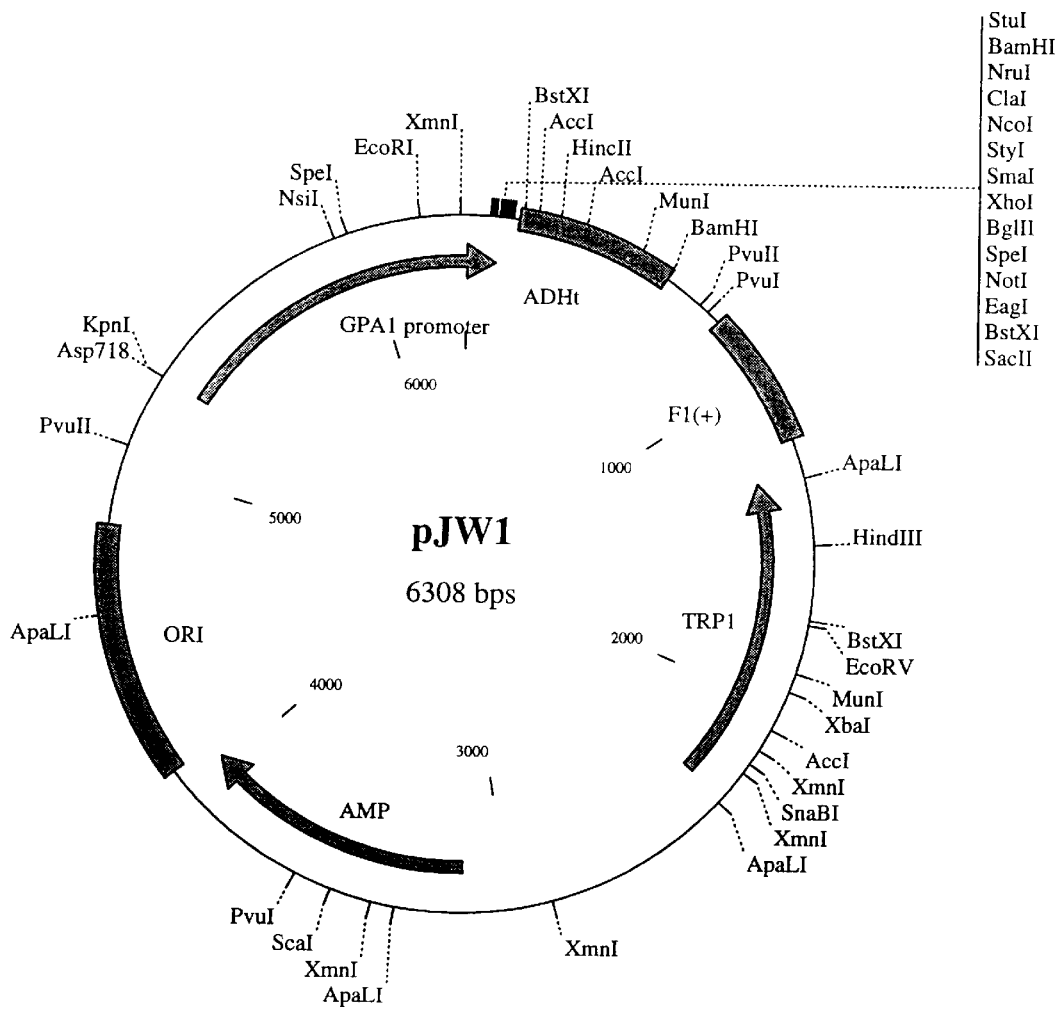
Figure 6C:
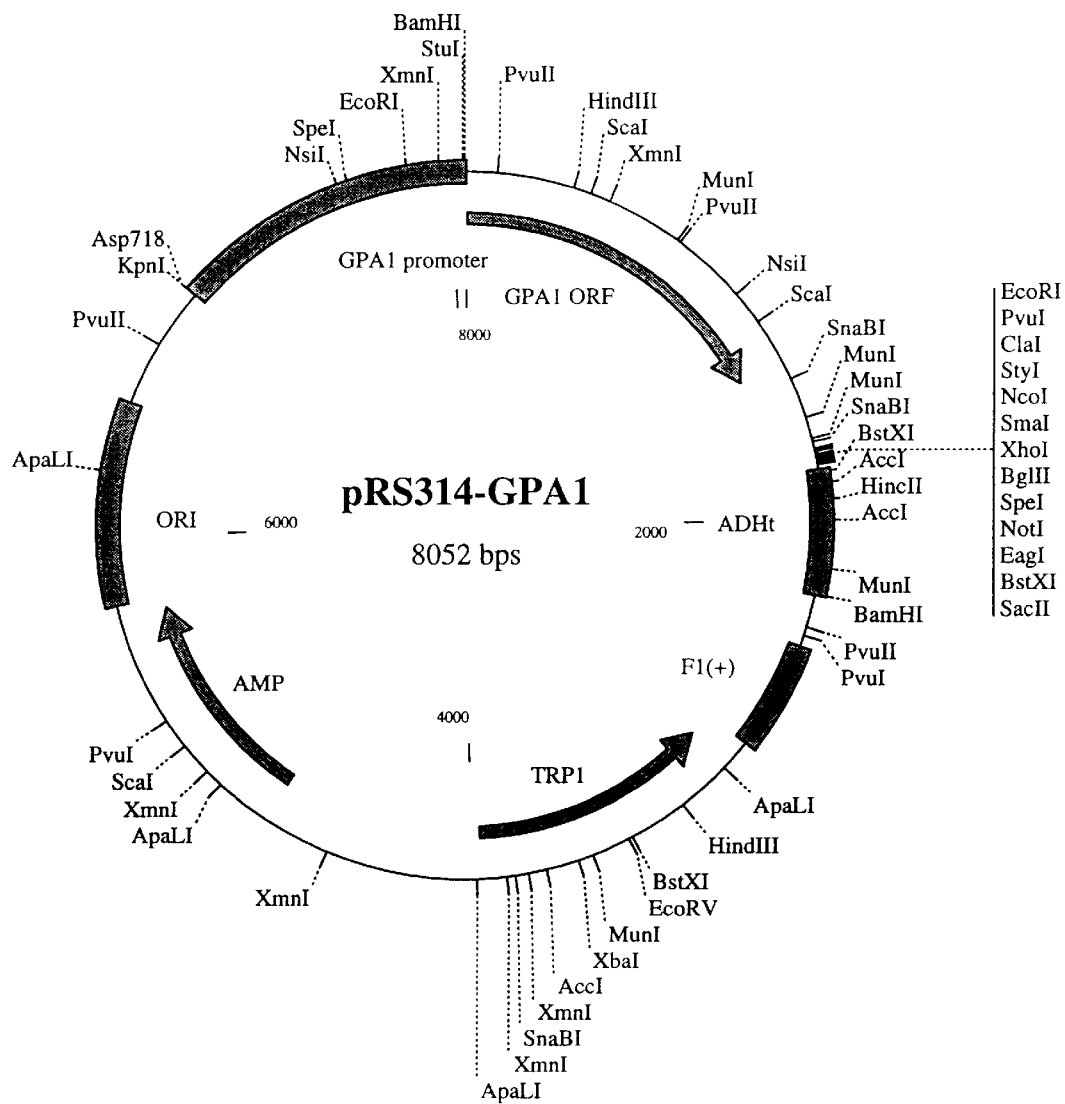

To create a construct for expression of sequences encoding G protein a subunits, a cassette consisting of the 1 Kb upstream region of the GPA1 gene (the GPA1 promoter), plus a multiple cloning site and the transcription terminator region of the ADH1 gene (ADHt) were inserted into the centromeric plasmid pRS314 (Stratagene), generating pJW1 (FIG. 6b). The GPA1 open reading frame was inserted into the NruI site of pJW1 to create the GPA1 expression plasmid pRS314-GPA1 (FIG. 6c).

Gpa1/Gα$_{i3}$ Chimera

Sequence encoding the chimeric $G_\alpha$ subunit Gpa1/$G_{\alpha 13}$ was derived from the plasmid pADC2-SCGi3. The chimera encoded by this plasmid is of a structure identical to that reported by Kang et al. (14) (with a BamHI site in the switch II domain) except that it contains the C-terminus of $G_{\alpha i3}$ rather than $G_{\alpha i2}$. The Gpa1/$G_{\alpha i3}$ expression construct used in this study was created by PCR amplification using oligodeoxynucleotide primers to incorporate NcoI and NotI restriction enzyme sites adjacent to the open reading frame.

Figure 6D:
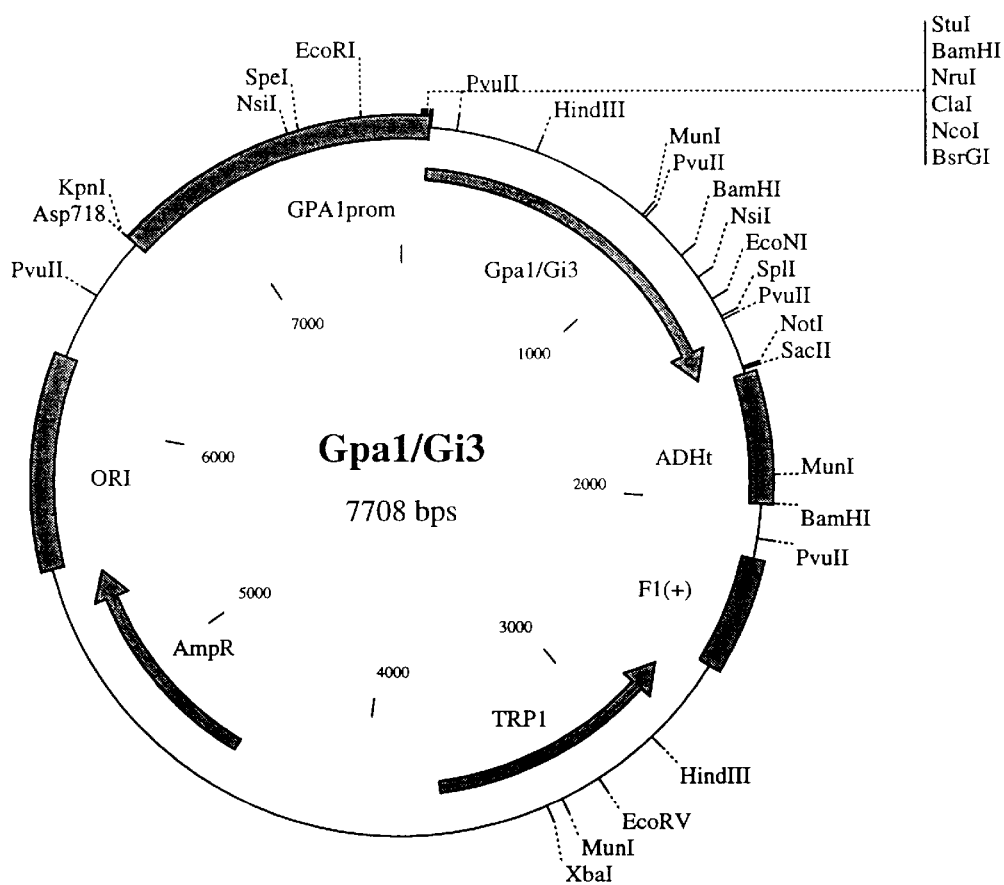
Figure 6E:
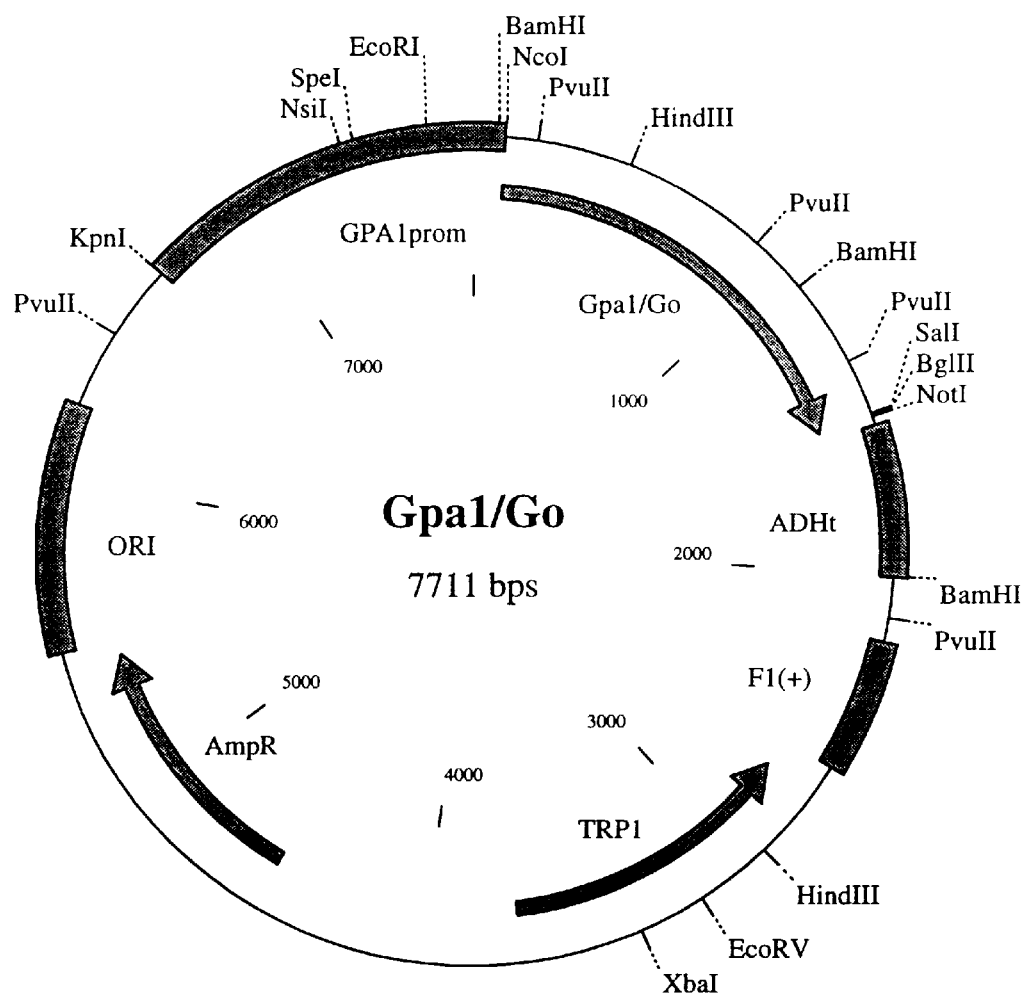
Figure 6F:
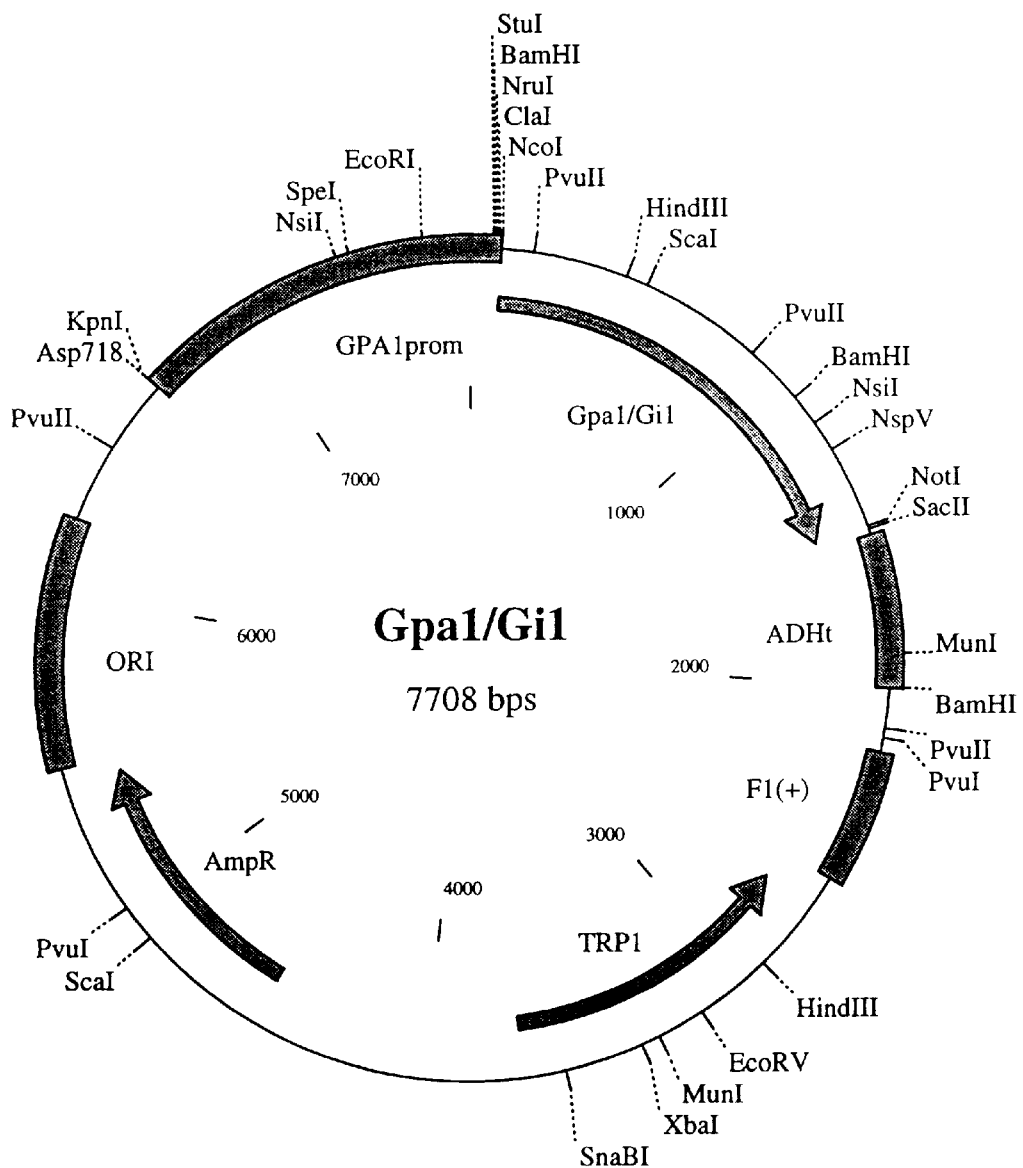
Figure 6G:
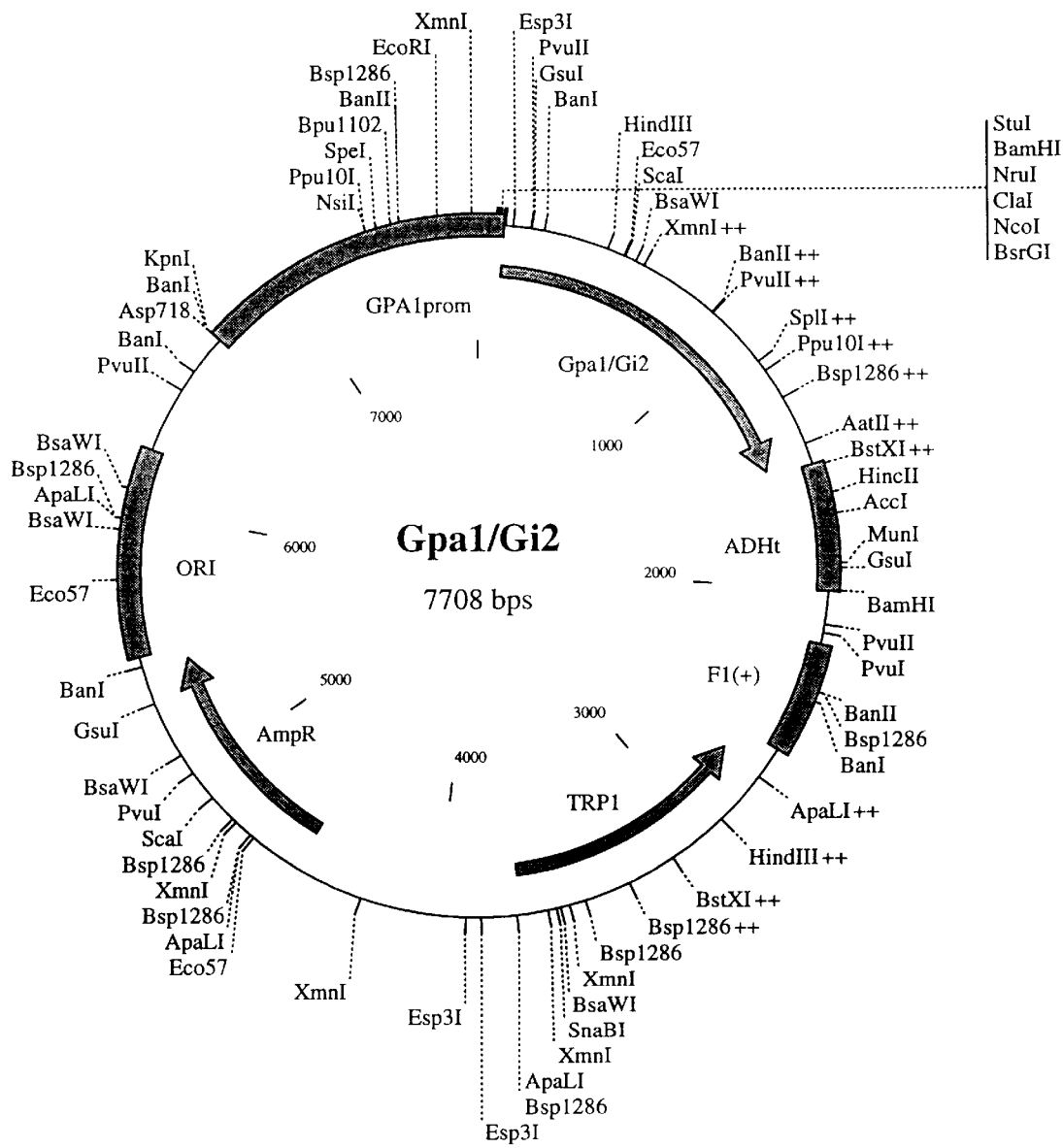

The sequence encoding the Gpa1/$G_{\alpha i3}$ chimera was inserted between the NcoI and NotI restriction enzyme sites of pJW1, to create the plasmid pRS314-Gpa1/$G_{\alpha i3}$ (FIG. 6d). Constructs to express the Gpa1/$G_{\alpha o}$, Gpa1/$G_{\alpha i1}$, Gpa1/$G_{\alpha i2}$ Gpa1/$G_{\alpha s}$ Gpa1/$G_{\alpha q}$ and Gpa1/$G_{\alpha 16}$ chimeras were derived from pRS314-Gpa1/$G_{\alpha i3}$ by replacing the $G_{\alpha i3}$-derived sequence (between the BamHI and NotI restriction enzyme sites) with sequences encoding corresponding C-terminal regions of $G_{\alpha o}$, $G_{\alpha i1}$, $G_{\alpha i2}$, $G_{\alpha s}$, $G_{\alpha q}$ and $G_{\alpha 16}$. Plasmid maps of pRS314-Gpa1/$G_{\alpha o}$, pRS314-Gpa1/$G_{\alpha i1}$, pRS314-Gpa1/$G_{\alpha i2}$, and pRS314-Gpa1/$G_{\alpha 16}$ are presented in FIGS. 6e, f, g and h, respectively.

$G_\alpha$ Transplants

The 'transplants', which had amino acid modifications the extreme C-terminus of Gpa1p, were generated in three steps. First, the AflII site located in the GPA1 promoter of pRS314GPA1 was removed by blunt-ending with Klenow and religation. Next, codon 467 of GPA1 was altered from AAA to AAG by site-directed mutagenesis, which was carried out using the Quik-change kit (Stratagene). This nucleotide change introduced an AflII site without changing the encoded protein sequence. Finally, the AflII/XhoI fragment was replaced with oligodeoxynucleotide linkers created by annealing the pairs of oligodexoynucleotides shown in Table 1.

pathway was monitored by two reporter genes, FUS1-HIS3 and FUS1-lacZ which were integrated into the FUS1 and leu2 loci, respectively. The FAR1 gene was deleted by one-step gene replacement using a far1Δ::URA3 DNA construct, so that growth continued even under conditions which activated the pheromone response pathway. The SST2 gene was deleted by one-step gene replacement using a sst2Δ::URA3 DNA construct to prevent down-regulation of G protein signalling by the GTPase-activating function encoded by this gene. After each of these manipulations, the ura3 marker was recovered by transformation with a ura3Δ fragment consisting of the of the URA3 gene with an internal 243 bp (EcoRV to StuI) deletion, followed by 5-fluoro-orotic acid selection. The chromosomal GPA1 ($G_\alpha$) gene was deleted by one-step gene replacement using a gpa1Δ::ADE2 DNA construct.

The yeast strain MMY11 was derived from MMY9 by one-step gene replacement using a ste2Δ::G418$^R$ DNA construct, selecting for geneticin resistant colonies and confirming that resistant colonies failed to respond to the Ste2p agonist, α-factor.

Assays for Reporter Gene Expression

Agonists somatostatin (S-14), melatonin, serotonin, adenosine 5'-diphosphate (ADP) and uridine 5'-triphosphate (UTP) were obtained from Sigma. Alpha factor was synthesised by Peptide and Protein Research, Exeter, UK. 5'-N-Ethylcarboxamidoadenosine (NECA) was obtained from Research Biochemicals International.

Assay for FUS1-HIS3 Expression. Reverse halo assays were carried out by growing MMY9 cells to early stationary

TABLE 1

| Oligodeoxy-nucleotide | Sequence (5' to 3') | Transplant |
|---|---|---|
| Gqtop | TTAAGGAATACAACCTAGTTTGAATTCCG SEQ ID NO:1 | Gpa1/$G_{\alpha q}$ |
| Gqbtm | TCGACGGAATTCAAACTAGGTTGTATTCC SEQ ID NO:2 | |
| Gstop | TTAAGCAATACGAACTATTGTGAATTCCG SEQ ID NO:3 | Gpa1/$G^{\alpha s}$ |
| Gsbtm | TCGACGGAATTCACAATAGTTCGTATTGC SEQ ID NO:4 | |
| Gotop | TTAAGGGTTGTGGCTTGTACTGAATTCCG SEQ ID NO:5 | Gpa1/$G_{\alpha o}$ |
| Gobtm | TCGACGGAATTCAGTACAAGCCACAACCC SEQ ID NO:6 | |
| Gi1top | TTAAGGATTGTGGTTTGTTTTGAATTCCG SEQ ID NO:7 | Gpa1/$G_{\alpha i1}$ |
| Gi1btm | TCGACGGAATTCAAAACAAACCACAATCC SEQ ID NO:8 | |
| Gi3top | TTAAGGATGTGGTTTGTACTGAATTCCG SEQ ID NO:9 | Gpa1/$G_{\alpha i3}$ |
| Gi3btm | TCGACGGAATTCAGTACAAACCACATTCC SEQ ID NO:10 | |
| Gztop | TTAAGTATATAGGCTTGTGTTGAATTCCG SEQ ID NO:11 | Gpa1/$G_{\alpha z}$ |
| Gzbtm | TCGACGGAATTCAACACAAGCCTATATAC SEQ ID NO:12 | |
| G12top | TTAAGGATATTATGTTGCAATGAATTCCG SEQ ID NO:13 | Gpa1/$G_{\alpha 12}$ |
| G12btm | TCGACGGAATTCATTGCAACATAATATCC SEQ ID NO:14 | |
| G13top | TTAAGCAATTGATGCTACAGTGAATTCCG SEQ ID NO:15 | Gpa1/$G_{\alpha 13}$ |
| G13btm | TCGACGGAATTCACTGTAGCATCAATTGC SEQ ID NO:16 | |
| G14top | TTAAGGAATTTAACTTGGTTTGAATTCCG SEQ ID NO:17 | Gpa1/$G_{\alpha 14}$ |
| G14btm | TCGACGGAATTCAAACCAAGTTAAATTCC SEQ ID NO:18 | |
| G16top | TTAAGGAAATTAACCTATTGTGAATTCCG SEQ ID NO:19 | Gpa1/$G_{\alpha 16}$ |
| G16btm | TCGACGGAATTCACAATAGGTTAATTTCC SEQ ID NO:20 | |
| Stoptop | TTAAGTGAGCGGCCGCGAATTCCG SEQ ID NO:21 | [truncated |
| Stopbtm | TCGACGGAATTCGCGGCCGCTCAC SEQ ID NO:22 | Gpa1p] |

Figure 5:
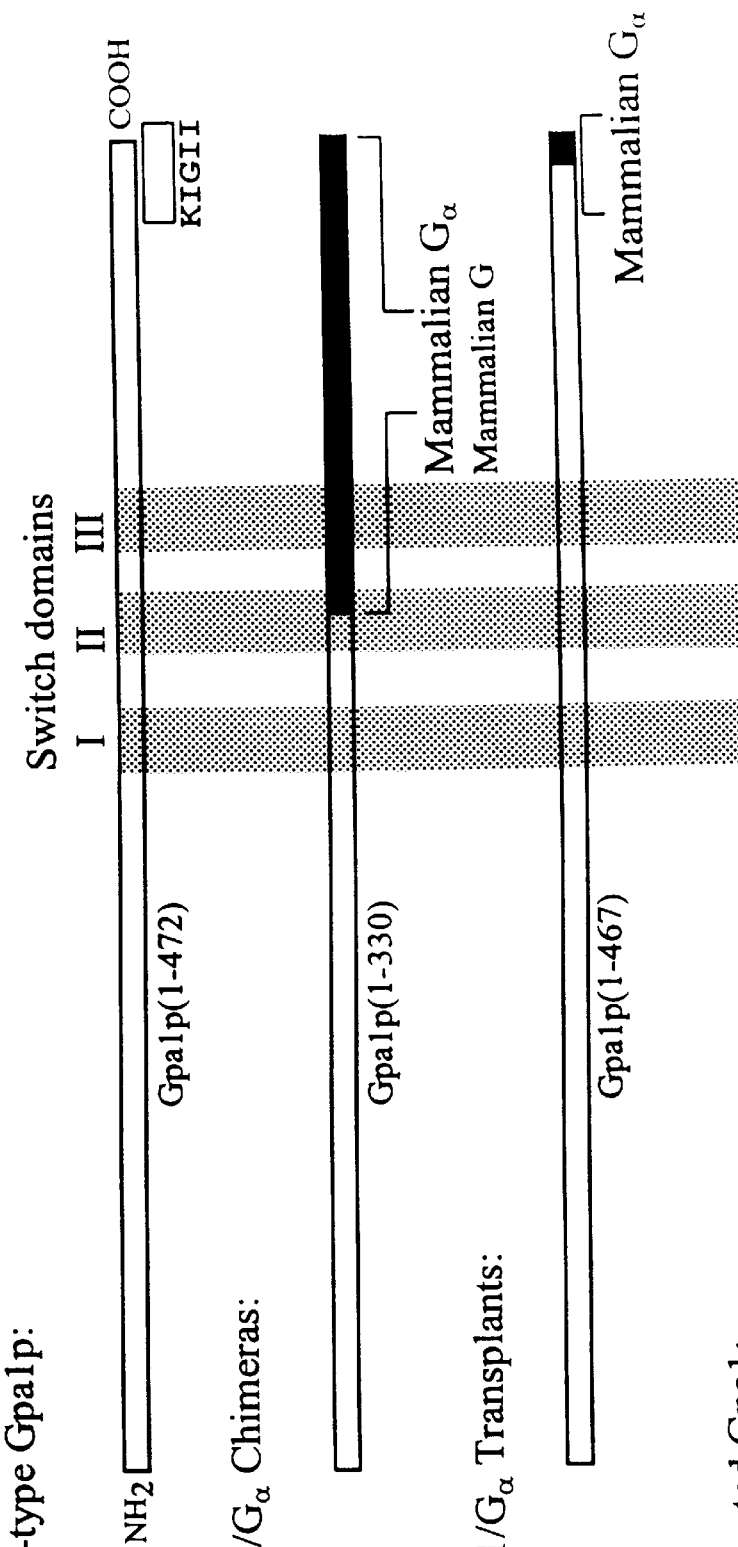
FIG. 5 is a diagrammatic representation of $G_\alpha$ subunit constructs used in this study. The switch domains are shaded. Numbers in parenthesis refer to amino acid numbers of wild-type $G_\alpha$ subunits. Gpa1/$G_\alpha$ chimeras in B) contained C-terminal regions (hatched) as follows: $G_{\alpha i1}$(212–354), $G_{\alpha i2}$ (213–355), $G_{\alpha i3}$ (212–354), $G_{\alpha 0}$ (213–354), $G_{\alpha 16}$ (221–374), $G_{\alpha s}$ (235–394), $G_{\alpha q}$ (211–353)

The resulting plasmids encoded in-frame fusions between amino acids 1 to 467 of Gpa1p and the 5 C-terminal acids of mammalian $G_\alpha$ subunits (FIG. 5c). A plasmid to express a truncated version of Gpap1 lacking the 5 C-terminal acids (FIG. 5d) was created by introducing a stop codon at codon position 468 by insertion of linkers as above (Table 1).

Yeast Strains

The yeast strain MMY9 was created to study the functional interactions between 7 transmembrane helix receptors and G proteins. This strain was derived from the common laboratory strain W303-1A (genotype: MATa his3 ade2 leu2 trp1 ura3 can1). Activation of the pheromone response phase ($OD_{600} \approx 4$) in liquid SC-glucose (2%) medium lacking tryptophan and uracil. A uniform layer of cells ($5 \times 10^7$) was plated to 22.5 cm by 22.5 cm bioassay dishes (Nunc) in 100 ml SC-glucose agar (1%) equilibrated to 50° C. This medium lacked tryptophan, uracil and histidine, and was supplemented with 10 mM 3-aminotriazole, and buffered to pH 7.0 with 0.1M sodium phosphate. Antibiotic discs were placed on the solidified agar, and a volume of agonist solution (1–5 μl) was applied to each disc. Plates were incubated at 30° C. for 3 days.

Assays for FUS1-lacZ Expression. β-galactosidase activities in cell extracts were measured with two assays. In the first assay (ONPG assay), cell extracts were incubated with the substrate ONPG as described by (37). Units were defined as $(A_{420} \times 1000)/(OD_{600} \times t \times v)$ (25). In the chemiluminescent assay, cells were grown to late logarithmic phase and diluted to 0.02 $OD_{600}$ in 100 µl SC-WH medium in the presence or absence of 1 µM α-factor in 96-well microtitre plates. After incubation (30° C.; 6 hours), 20 µl of cells were removed and mixed with 20 µl assay mix (125 mM sodium phosphate pH 7.6, 15 mM $MgSO_4$, 200 µM Galacton-Star β-galactosidase substrate (Tropix), 10% (v/v) Sapphire II (Tropix), 1 U/µl oxalyticase (Enzogenetics)). After incubation (30° C.; 1 hr) chemiluminescence was determined in a Top-count scintillation counter (Packard).

Assay for combined FUS1-lacZ and FUS1-HIS3 Expression. In vivo assays of reporter gene induction (CPRG assays) were carried out by suspending cells to 0.02 $OD_{600}$ in 200 µl SC-glucose (2%) lacking tryptophan, uracil and histidine. This medium was supplemented with agonists, and additionally 10 mM 3-aminotriazole and the β-galactosidase (lacZ) substrate chlorophenolred-β-D-galactopyranoside (CPRG; Boehringer) to a concentration of 0.1 mg/ml. To visualise the colour change reaction, the medium was buffered to pH 7 with 0.1 M sodium phosphate. The assay was conducted in a 96-well microtitre plate format. Plates were incubated for 24 hours without agitation, and absorbance at 570 nm was determined using a Victor microtitre plate reader (Wallac). $EC_{50}$ values (+/−standard error) were estimated by curve-fitting, using the Robosage software package.

Yeast strains used in this study:

| Strains | Genotype |
| --- | --- |
| W303-1A | MATa his3 ade2 leu2 trp1 ura3 can1 |
| MMY9 | W303-1A fus1:FUS1-HIS3 FUS1-lacZ::LEU2 far1Δ::ura3Δgpa1Δ::ADE2 sst2Δ::ura3Δ |
| MMY11 | MMY9 ste2Δ::G418$^R$ |

Experiment 1: Receptors Activating Yeast Pheromone Pathway

Figure 1:
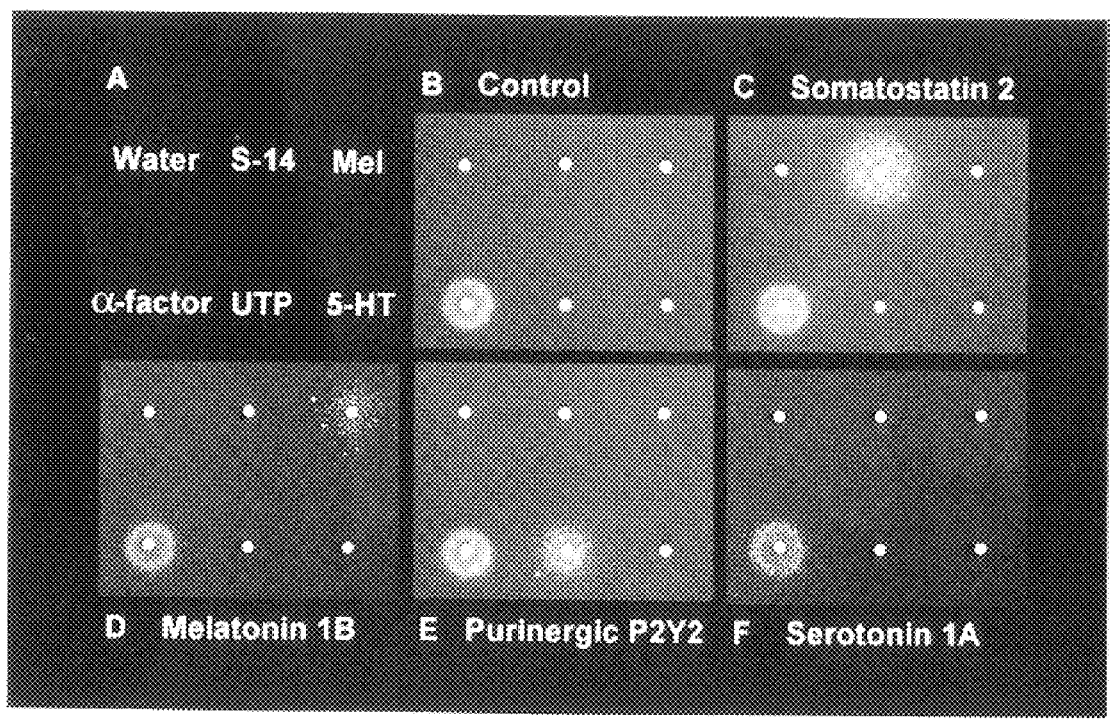
FIG. 1 shows agonist-dependent growth of the modified yeast (*S. cerevisiae*) strain MMY9. Cells expressing one of four human G protein-coupled receptors illustrate the ability of these receptors to interact with and activate the endogenous yeast $G_\alpha$ subunit (Gpa1p)
Figure 2A:
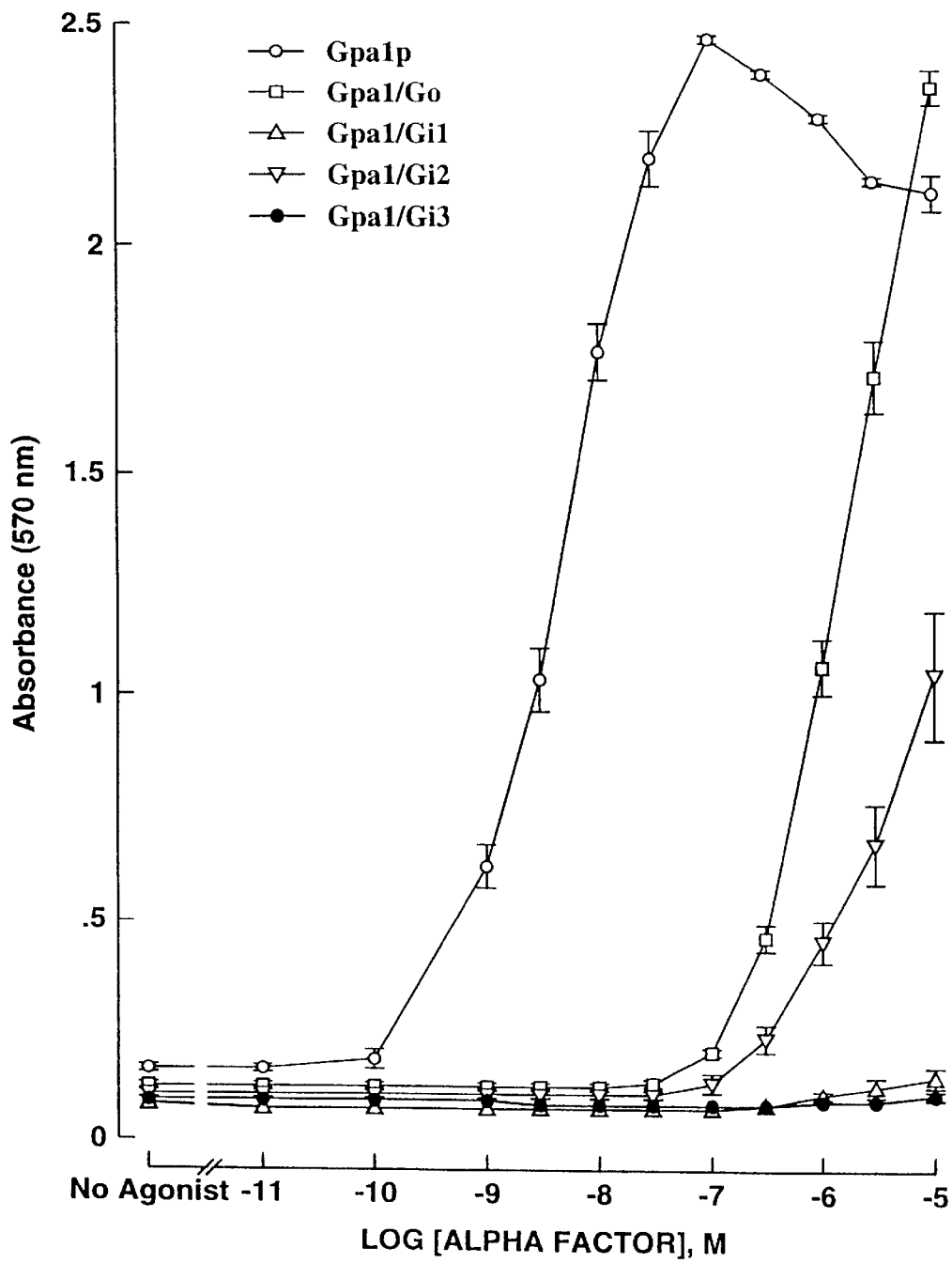
FIGS. 2a–d show induction of the FUS1-lacZ reporter gene in response to receptor agonists using cells expressing receptor plus different modified $G_\alpha$ subunits.
Figure 2B:
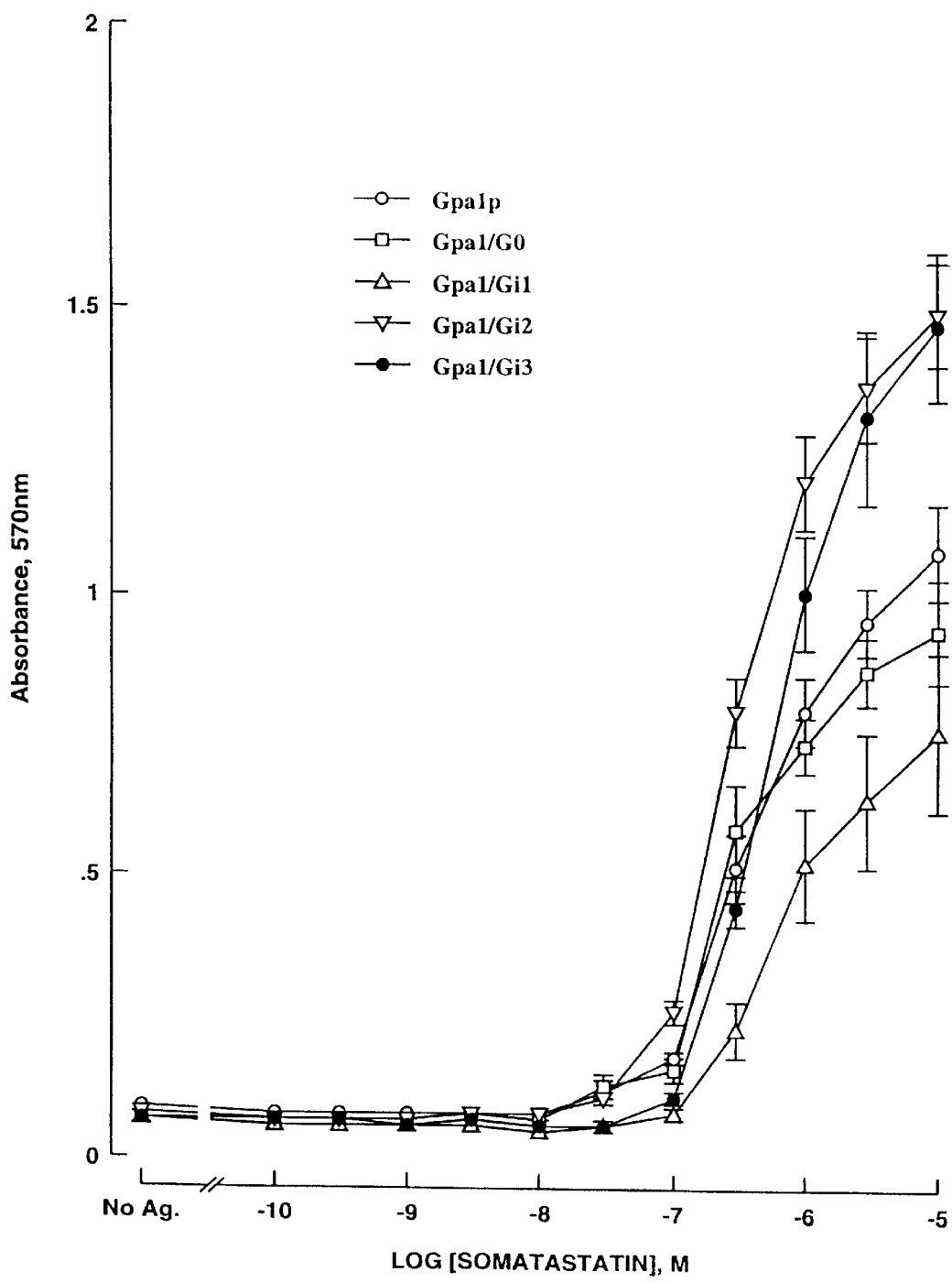
Figure 2C:
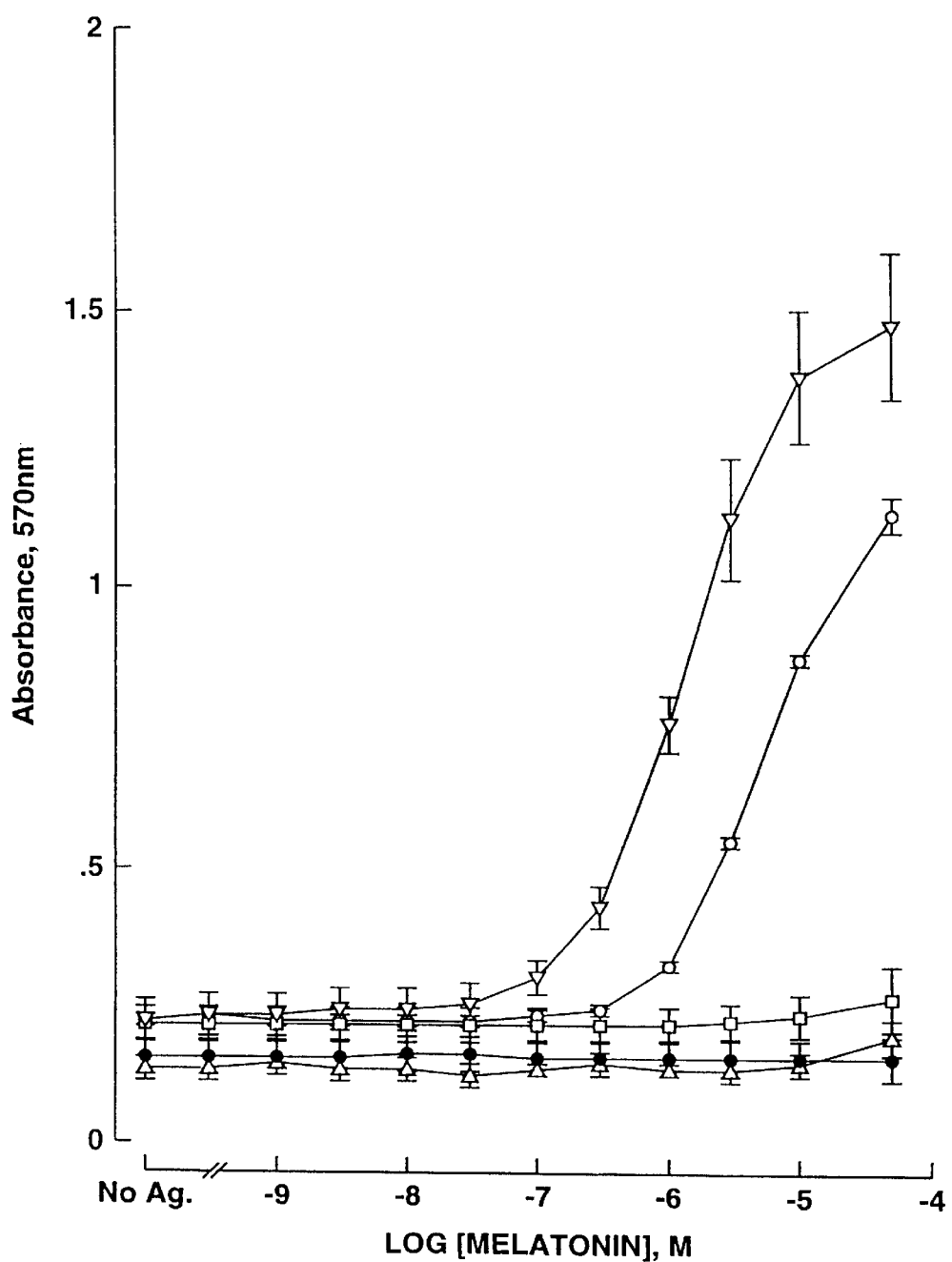
Figure 2D:
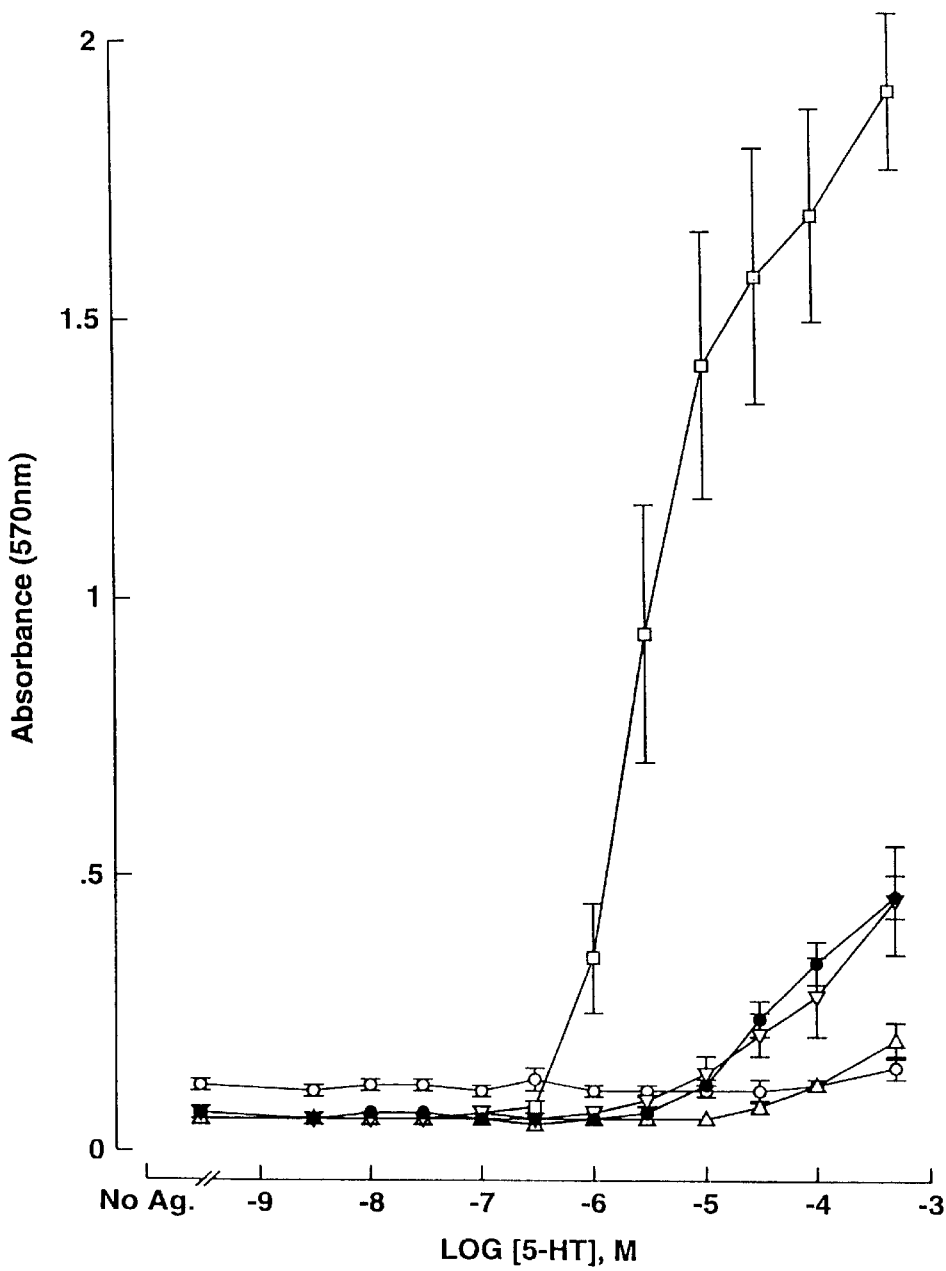

This experiment used four human G protein-coupled receptors as examples of receptors capable of activating the yeast pheromone response pathway. The four receptors were: the melatonin $ML_{1B}$ receptor, the serotonin $5HT_{1A}$ receptor, the somatostatin $SST_2$ receptor and the purinergic nucleotide receptor, $P2Y_2$. These receptors were expressed in yeast strain MMY9 described above. This strain was deleted for SST2, FAR1 and GPA1 but retained the endogenous α-factor receptor encoded by STE2. Activation of the pheromone response pathway was monitored with two integrated reporter genes: FUS1-HIS1 allowing a growth readout in medium lacking histidine, and FUS1-lacZ allowing a β-galactosidase readout. These assays are described herein above. We initially investigated signalling of these receptors via the endogenous yeast heterotrimeric G protein (Gpa1p/Ste4p/Ste18p). Receptors were expressed in yeast strain MMY9 from the strong PGK promoter, using high copy number episomal vectors. In FIG. 1, panels A–F show a reverse halo assay performed using MMY9 cells co-transformed with the plasmid pRS314-GPA1 (panels B to F), which expresses the wild-type GPA1 gene and, in addition, with either a receptor expression construct or vector, as follows: pDT-PGK (vector; panel B); pFL61-SST$_2$ (panel C); pDT-PGK-ML$_{1B}$ (panel D); pDT-PGK-P2Y$_2$ (panel E); pDT-PGK-5-HT$_{1A}$ (panel F). Agonist-dependent activation of FUS1-HIS3 was determined by reverse halo assay in which agonists were applied to the filter discs in the arrangement shown in panel A, in quantities as follows: 3 nmol of somatostatin-14 (S-14); 40 nmol of melatonin (Mel); 3 nmol of α-factor; 100 nmol of UTP; 40 nmol of serotonin (5-HT). As expected, treatment of MMY9 cells with the yeast pheromone, α-factor, stimulates the endogenous yeast receptor Ste2p, resulting in increased expression of FUS1-HIS3 to enable a halo of cell growth in the absence of histidine (FIG. 1, Panel B). Similarly, MMY9 cells expressing the ML$_{1B}$ receptor (panel D) activated FUS1-HIS3 in response to melatonin, as well as in response to α-factor. Cells expressing the SST$_2$ receptor (panel C) responded to somatostatin, and cells expressing the P2Y$_2$ receptor (panel E) responded to the agonist UTP. The zones of cell growth in FIG. 1 are comparable in size, although different molar quantities of agonist were required for each receptor. Thus, the ML$_{1B}$, SST$_2$ and P2Y$_2$ receptors can couple to the yeast pheromone response pathway, via activation of the endogenous $G_α$, Gpa1p. MMY9 cells transformed with the 5-HT$_{1A}$ receptor expression construct did not activate FUS1-HIS3 in response to the agonist serotonin, suggesting that this receptor interacts poorly or cannot functionally interact with Gpa1p.

Experiment 2: Yeast/Mammalian Chimera Coupling to Receptors

This experiment illustrates that, for certain receptors, the efficiency of coupling to the yeast pheromone response pathway can be enhanced by creating chimeras between yeast and mammalian $G_α$ subunits. A series of chimeric $G_α$ subunits was generated in which the C-terminal domain (C-terminal 142 amino acids) of Gpa1p was replaced with corresponding regions of rat $G_{αo}$, $G_{αi1}$, $G_{αi2}$ and $G_{αi3}$ (FIG. 5b). To achieve an appropriate stoichiometry of G protein subunits, the chimeras were encoded on centromeric plasmids and expressed from the promoter of the GPA1 gene. This avoids quenching of the $G_β/G_γ$-mediated signal, due to excess $G_α$ (33). These constructs were used in an experiment in which MMY9 cells were cotransformed with pairs of plasmids, one expressing a $G_α$ subunit and the second either vector (pDT-PGK) or one of the receptor expression constructs pFL61-SST$_2$, pDT-PGK-ML$_{1B}$, pDT-PGK-P2Y2 or pDT-PGK-5-HT$_{1A}$. Agonist-dependent activation of FUS1-lacZ was determined by incubating cells in medium supplemented with the chromogenic, cell-permeant β-galacosidase (lacZ) substrate, chlorophenolred-β-D-galactopyranoside (CPRG; Boehringer Mannheim). The extent of conversion of this substrate after 24 hr incubation at 30° C. was determined by spectrophotometry and the results for the yeast $G_α$ and the four chimeras are shown in FIGS. 2a–d: 2a Ste2p receptor (pDT-PGK—transformed cells); 2b, SST$_2$ receptor (pFL61-SST$_2$); 2c ML$_{1B}$ receptor (pDT-PGK-ML$_{1B}$); 2d 5-HT$_{1A}$ receptor (pDT-PGK-5-HT$_{1A}$).

As expected, α-factor stimulated the endogenous Ste2p receptor resulting in induction of FUS1-lacZ and provoking the strongest response with Gpa1p (EC$_{50}$; 5.2+/−0.4 nM). This value is consistent with the reported affinity of Ste2p for α-factor peptide (K$_d$; 17 nM) (3). MMY9 cells expressing the Gpa1/G$_{αo}$ and Gpa1/G$_{αi2}$ chimeras also induced FUS1-lacZ in response to high concentrations of α-factor, but dose-response curves were displaced rightwards by at least two log units, suggesting that the Ste2p receptor interacts less efficiently with these chimeras than with wild-type Gpa1p. MMY9 cells expressing Gpa1/G$_{αi1}$ or Gpa1/G$_{αi3}$ chimeras did not induce FUS1-lacZ in response to α-factor. In contrast, the somatostatin SST$_2$ receptor was coupled to the pheromone response pathway by all the G$_{αi}$ chimeras (EC$_{50}$ values: 430+/−44 nM; 300+/−38 nM;

650+/−65 nM; 300+/−22 nM; and 630+/−30 nM for respectively Gpa1p, Gpa1/G$_{\alpha 0}$, Gpa1/G$_{\alpha i1}$, Gpa1/G$_{\alpha i2}$, and Gpa1/G$_{\alpha i3}$). This confirms that the chimeric G$_\alpha$ subunits are functional, and suggests that failure of receptors to couple to the pheromone response pathway is due to incompatibility with the G$_\alpha$ C-terminal region. We confirmed that the chimera proteins were produced at levels comparable to wild-type Gpa1p by quantitative Western blotting (data not shown), using a polyclonal antibody directed against the N-terminus of Gpa1p which is common to all these proteins.

Of the other receptors, 5-HT$_{1A}$ and ML$_{1B}$ both exhibited more efficient coupling to the pheromone response pathway in cells expressing chimeric G$_\alpha$ subunits than those expressing Gpa1p. The 5-HT$_{1A}$ receptor adopts a conformation in yeast capable of activating Gpa1/G$_{\alpha 0}$, supporting the hypothesis from Experiment 1 that this receptor is incompatible or poorly compatible with Gpa1p. Strikingly, the receptors are specific for particular chimeras, for example ML$_{1B}$ activates Gpa1/G$_{\alpha i2}$ but not Gpa1/G$_{\alpha i3}$, even though these chimeras differ at just 14 amino acid positions, and levels of expression are similar in each case. When signalling was mediated by wild-type Gpa1p, FUS1-lacZ was induced to a lesser extent by P2Y$_2$ than the other receptors (data not shown), consistent with the requirement for greater molar quantities of agonist to give a similar zone of growth in the reverse halo assay (FIG. 1). The P2Y2 agonist response was not enhanced by any of the G$_{\alpha i}$ chimeras (data not shown).

Experiment 3: Chimeras with C-terminal Regions of G$_{\alpha 16}$

Figure 6H:
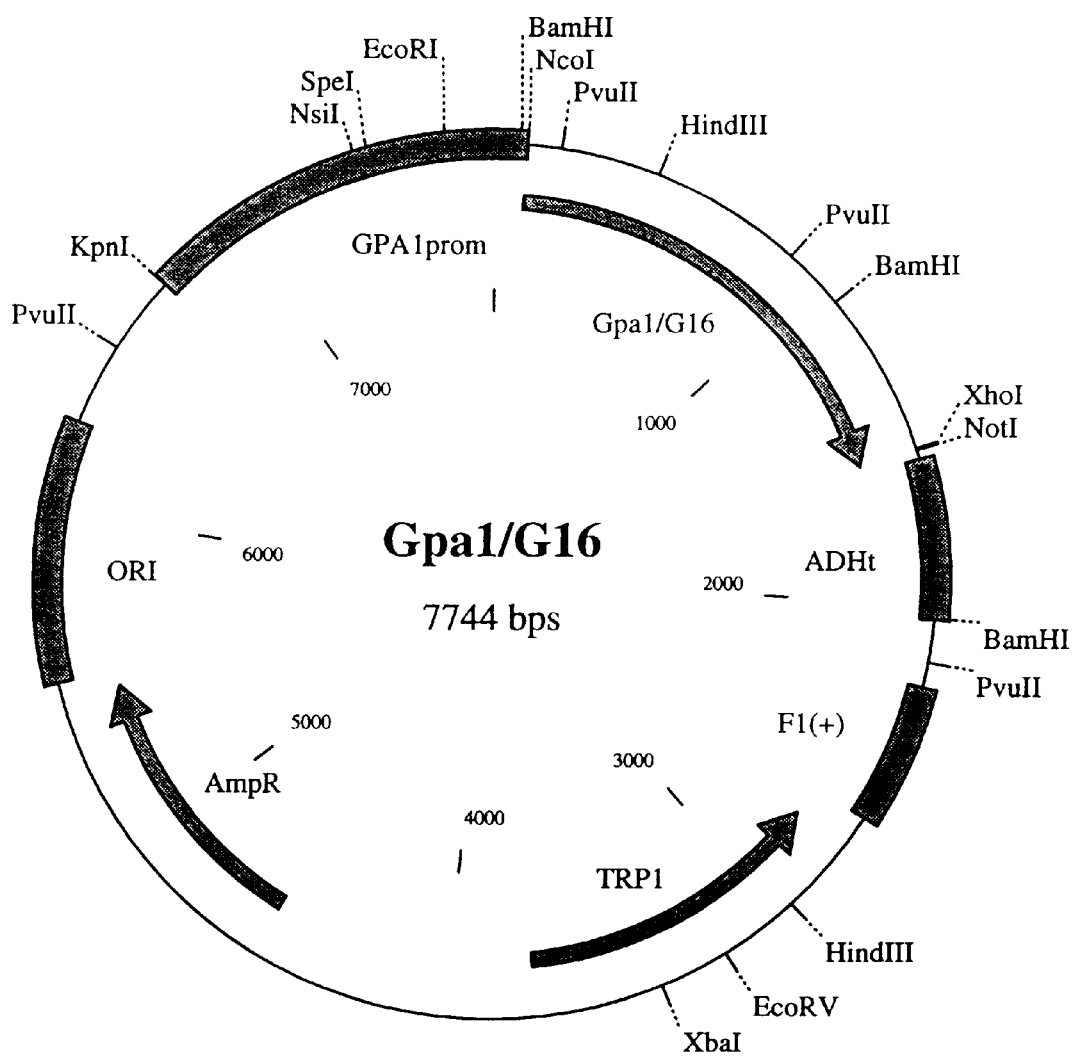

The G$_{\alpha 15}$/G$_{\alpha 16}$ subunits are reported to interact with a much broader range of receptors than is typical for a G$_\alpha$ subunit, and have the ability to couple receptors which normally interact with G$_{\alpha i}$, G$_{\alpha s}$ or G$_{\alpha q}$ (26). A Gpa1/G$_{\alpha 16}$ C-terminal domain chimera, if it exhibited similar properties to full-length G$_{\alpha 16}$, might be expected to couple diverse receptors to the pheromone response pathway. We constructed a plasmid encoding a Gpa1/G$_{\alpha 16}$ C-terminal domain chimera (pRS314-Gpa1/G$_{\alpha 16}$; FIG. 5b); FIG. 6h) derived from the same centromeric vector as used for expression of functional chimeras described above. The level of FUS1-LacZ induction in MMY9 cells expressing the Gpa1/G$_{\alpha 16}$ chimera was determined by preparing cell extracts, and incubating them with the LacZ substrate o-Nitrophenyl β-D-galactopyranoside (ONPG; see Materials and Methods). Gpa1/G$_{\alpha 16}$ reduced FUS1-LacZ expression resulting in β-galactosidase activity of 79+/−8 units (Table 2). This level was intermediate between the activity of control cells transformed with vector (239+/−30 units), in which the pathway is constitutively activated due to the absence of G$_\alpha$, and the basal activity in cells producing wild-type Gpa1p (19+/−4 units). Therefore, the pheromone response pathway was partially activated, suggesting that this construct, which directs expression of Gpa1/G$_{\alpha 16}$ from the GPA1 promoter, fails to sequester all free G$_\beta$/G$_\gamma$.

TABLE 2

Gpa1/G$_{\alpha 16}$ binds yeast G$_\beta$/G$_\gamma$ but fails to support coupling of the Ste2p receptor.

| G protein | Promoter | No Alpha Factor | Plus Alpha Factor | n |
|---|---|---|---|---|
| Vector | | 239 +/− 30 | 224 +/− 44 | 5 |
| GPA1 | GPA1 | 19 +/− 4 | 273 +/− 49 | 3 |
| GPA1/G16 | GPA1 | 79 +/− 8 | 79 +/− 4 | 3 |
| GPA1/G16 | TEF1 | 23 +/− 5 | 24 +/− 8 | 5 |
| GPA1/G16 | GPD1 | 16 +/− 4 | 13 +/− 4 | 3 |

Figure 3:
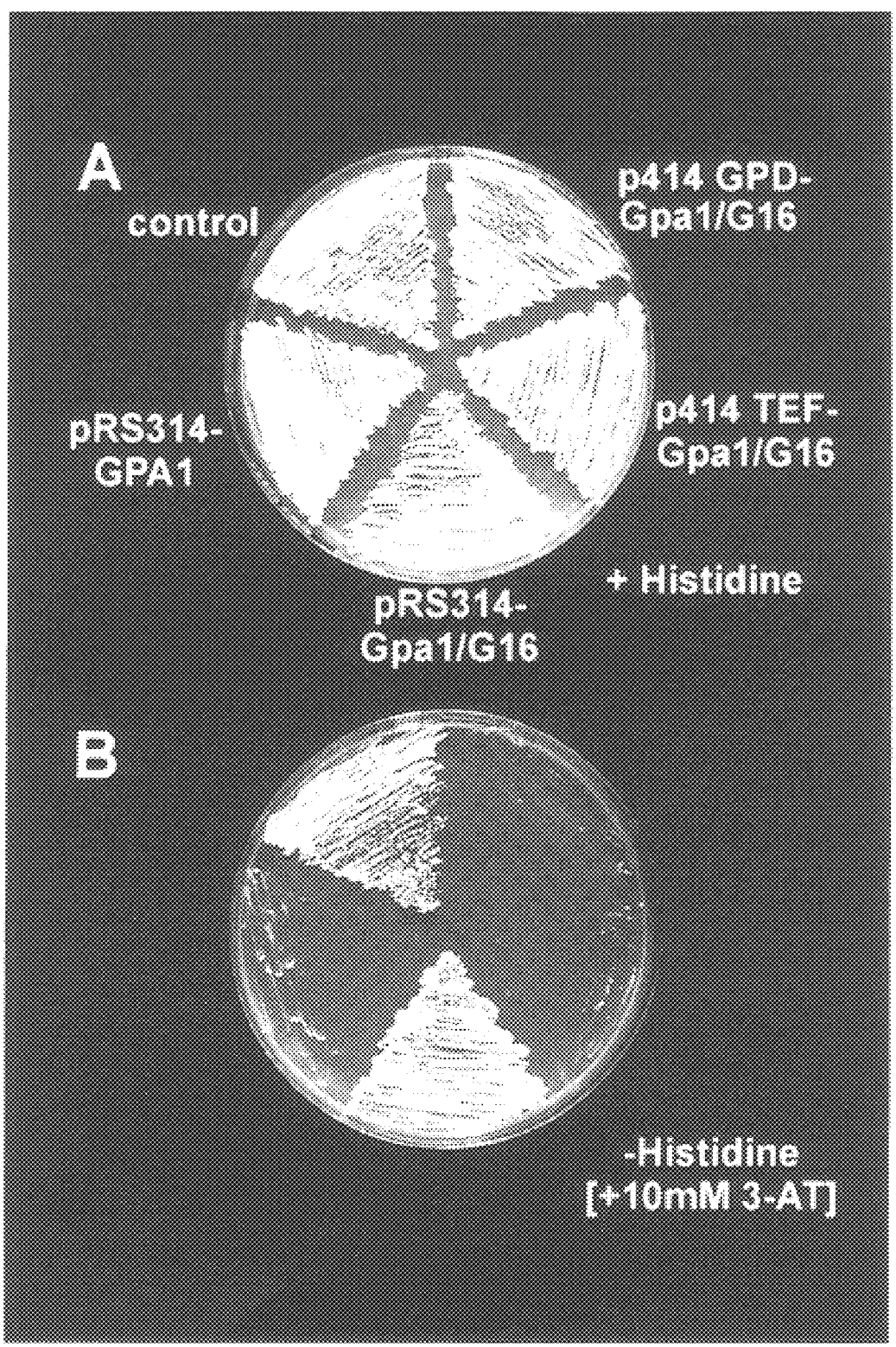
FIG. 3 shows that constructs which express a Gpa1/$G_{\alpha 16}$ chimera (containing a large C-terminal domain derived from $G_{\alpha 16}$) reduce FUS1-HIS3 reporter gene expression to basal levels.

We made further constructs to express Gpa1/G$_{\alpha 16}$ from the stronger TEF1 and GPD1 promoters. These reduced FUS1-lacZ expression to levels comparable to those in Gpa1p-producing cells (Table 1). In FIG. 3, MMY9 cells transformed with the different Gpa1/G$_{\alpha 16}$ expression constructs, or control plasmids were streaked to a non-selective agar plate supplemented with histidine (panel A) and to a selective agar plate lacking histidine and supplemented with 3-aminotriazole (panel B). The TEF-Gpa1/G$_{\alpha 16}$ and GPD-Gpa1/G$_{\alpha 16}$ expression constructs reduced FUS1-HIS3 reporter gene expression to prevent growth on histidine-selective medium in common with the positive control plasmid (pRS314-GPA1), which expresses wild-type GPA1. In contrast, the Gpa1/G$_{\alpha 16}$ expression construct which utilised the GPA1 promoter (pRS314-Gpa1/G$_{\alpha 16}$) failed to reduce FUS1-HIS3 expression sufficiently to prevent growth under histidine-selective conditions, similar to the situation with vector-transformed cells (control). This result agrees with the ONPG assay results tabled above, therefore, the two reporter genes, FUS1-lacZ and FUS1-HIS3, behave similarly.

With none of the Gpa1/G$_{\alpha 16}$ expression constructs, however, did the Ste2p receptor appear to be coupled to the pheromone response pathway, because treatment of cells with α-factor did not induce FUS1-LacZ (Table 1). MMY9 cells expressing the other receptors (ML$_{1B}$, 5-HT$_{1A}$, P2Y$_2$, or SST$_2$) in combination with Gpa1/G$_{\alpha 16}$ also did not exhibit agonist-dependent induction of FUS1-LacZ (data not shown). Therefore, even though Gpa1/G$_{\alpha 16}$ can prevent the yeast G$_\beta$/G$_\gamma$ particle from activating the pheromone response pathway, presumably by assembling into a G protein trimer, no free G$_\beta$/G$_\gamma$ is released in the presence of activated receptors. Clearly, the approach of constructing this type of chimera, containing a large C-terminal domain derived from a mammalian G$_\alpha$ subunit fused to the N-terminal region of Gpa1p, is not generally applicable to all G$_\alpha$ subunits, but is successful with some G$_\alpha$ subunits (including the G$_{\alpha i}$ family and G$_{\alpha s}$) but not others (such as G$_{\alpha 16}$). The Gpa1/G$_{\alpha 16}$ chimera lacks the important property of full-length G$_{\alpha 16}$, that of coupling a much broader range of receptors than other G$_\alpha$ subunits. This experiment confirms that Gpa1/G$_{\alpha 16}$ C-terminal domain chimeric protein is produced in cells, and thus that its failure to couple G protein-coupled receptors to the pheromone response pathway is likely to be due to incompatibility between receptor and this G$_\alpha$ subunit.

A Gpa1/G$_{\alpha s}$ chimera has been reported to couple the growth hormone releasing hormone receptor (12) when expressed from the strong constitutive promoter of the yeast phosphoglycerate kinase (PGK1) gene. We constructed Gpa1/G$_{\alpha s}$ and Gpa1/G$_{\alpha q}$ chimeras similar to those described above (FIG. 5b) and expressed them in MMY9 cells from the promoter of the GPA1 gene. We assayed FUS1-LacZ activity in these cells using a chemiluminescent assay, rather than the ONPG assay described above. Results are presented in Table 3. As expected from the previous experiments, cells expressing Gpa1/G$_{\alpha 16}$ from the GPA1 promoter exhibited significantly higher activities than control cells expressing Gpa1p. Gpa1/G$_{\alpha s}$ and Gpa1/G$_{\alpha q}$ chimeras are similar to Gpa1/G$_{\alpha 16}$ in that they also have significantly higher activities than control cells expressing Gpa1p. In contrast, cells expressing Gpa1/G$_{\alpha 0}$, Gpa1/G$_{\alpha i1}$, Gpa1l/G$_{\alpha i2}$, or Gpa1/G$_{\alpha i3}$ from the GPA1 promoter as expected contained activities comparable to control cells expressing Gpa1p. In this experiment only wild-type Gpa1p and the Gpa1/G$_{\alpha 0}$ chimera coupled the Ste2p receptor, as shown by increased FUS1-LacZ levels in cells incubated with 1 μM α-factor. This is consistent with the results of the CPRG assay above. This experiment further confirms that the Gpa1/G$_{\alpha 0}$, Gpa1/

$G_{\alpha i1}$, Gpa1/$G_{\alpha i2}$, or Gpa1/$G_{\alpha i3}$ chimeras may be expressed from the GPA1 promoter and result in sufficiently low activation of the pheromone response pathway in the absence of activated receptor to be able to detect coupling, but that the Gpa1/$G_{\alpha s}$, Gpa1/$G_{\alpha q}$ and Gpa1/$G_{\alpha 16}$ chimeras may not.

TABLE 3

Activity of the pheromone response pathway in MMY9 cells expressing chimeric $G_\alpha$ subunits

| $G_\alpha$ subunit | FUS1-LacZ Activity | |
|---|---|---|
| | No α-factor | 1 μM α-factor |
| [vector] | 8.7 ± 2.0 | 7.4 ± 1.6 |
| Gpa1p | 0.73 ± 0.25 | 27.2 ± 1.7 |
| Gpa1/$G_{\alpha i1}$ | 0.71 ± 0.2 | 0.68 ± 0.15 |
| Gpa1/$G_{\alpha i2}$ | 0.66 ± 0.33 | 0.67 ± 0.34 |
| Gpa1/$G_{\alpha i3}$ | 0.50 ± 0.22 | 0.76 ± 0.23 |
| Gpa1/$G_{\alpha o}$ | 0.44 ± 0.12 | 0.75 ± 0.069 |
| Gpa1/$G_{\alpha 16}$ | 3.6 ± 1.9 | 3.6 ± 1.5 |
| Gpa1/$G_{\alpha s}$ | 3.1 ± 2.0 | 5.0 ± 3.0 |
| Gpa1/$G_{\alpha i q}$ | 8.2 ± 3.9 | 9.6 ± 4.1 |

Values are mean ±SD light units (×10⁶ cps) in the chemiluminescent β-galactosidase assay. n≥5.

Experiment 4: Transplant Approach

Figure 4A:
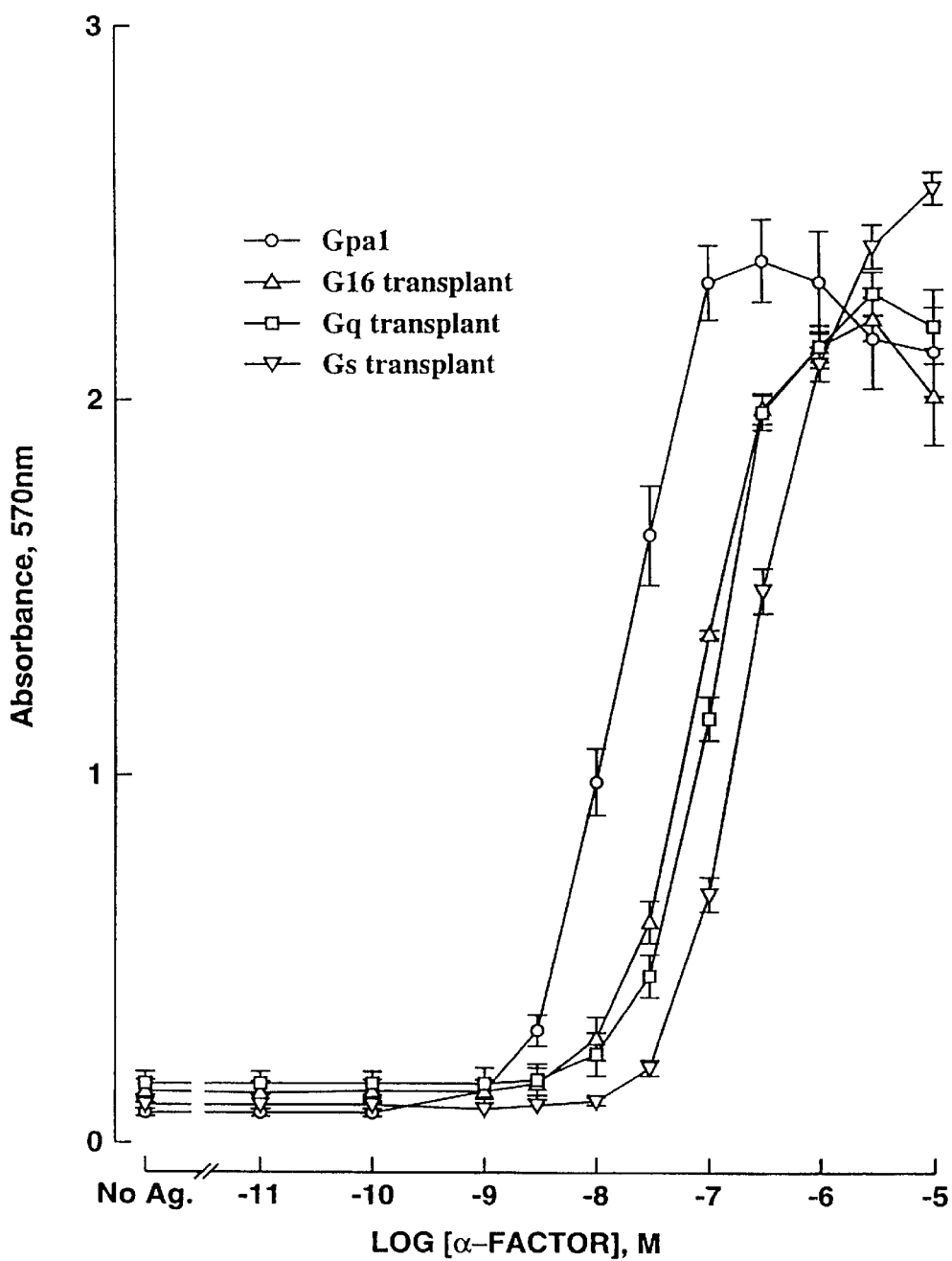
FIGS. 4a–d show agonist-dependent activation of the FUS1-lacZ reporter gene by receptor agonists, mediated by Gpa1p modified at the C-terminal five residues (the transplants)
Figure 4B:
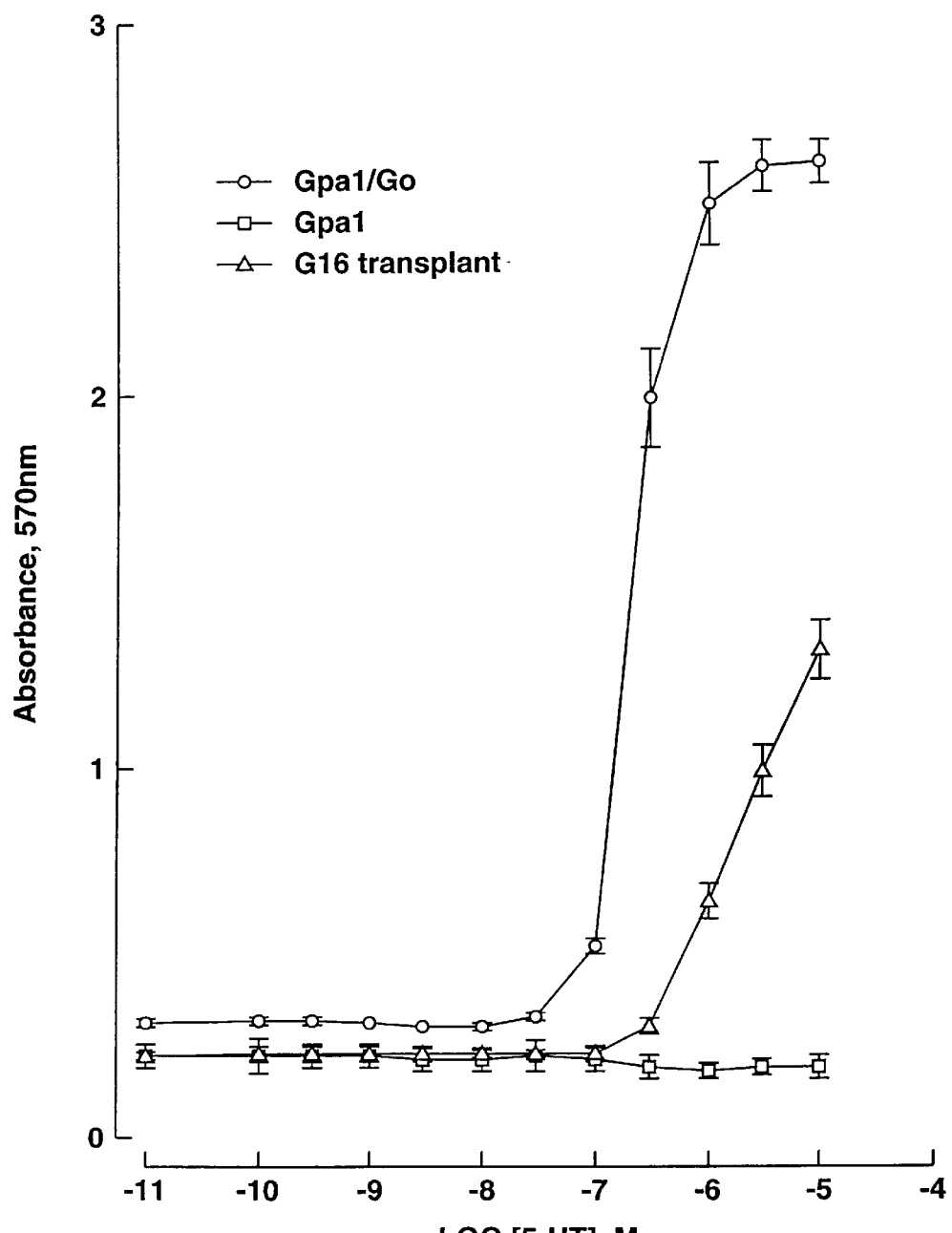
Figure 4C:
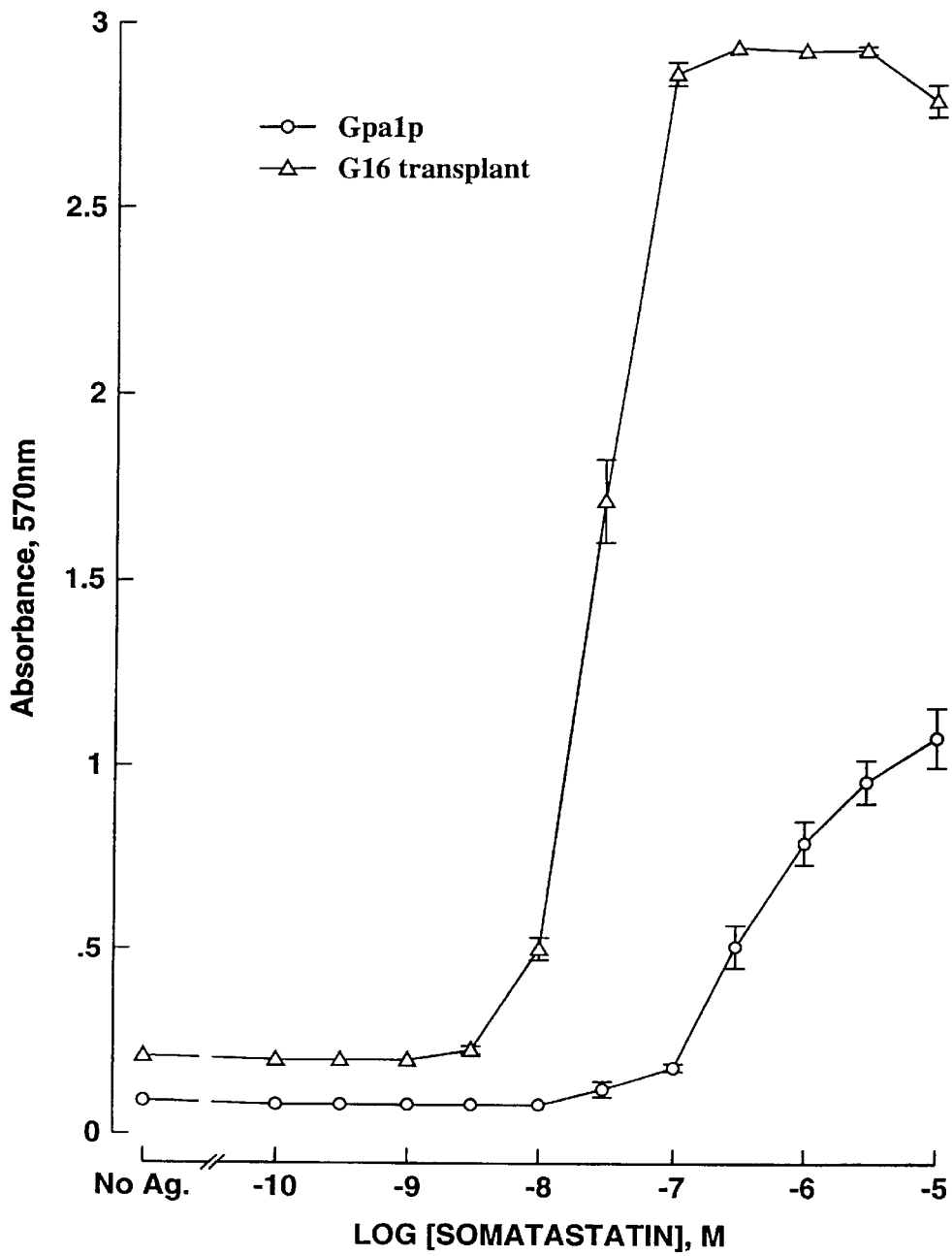
Figure 4D:
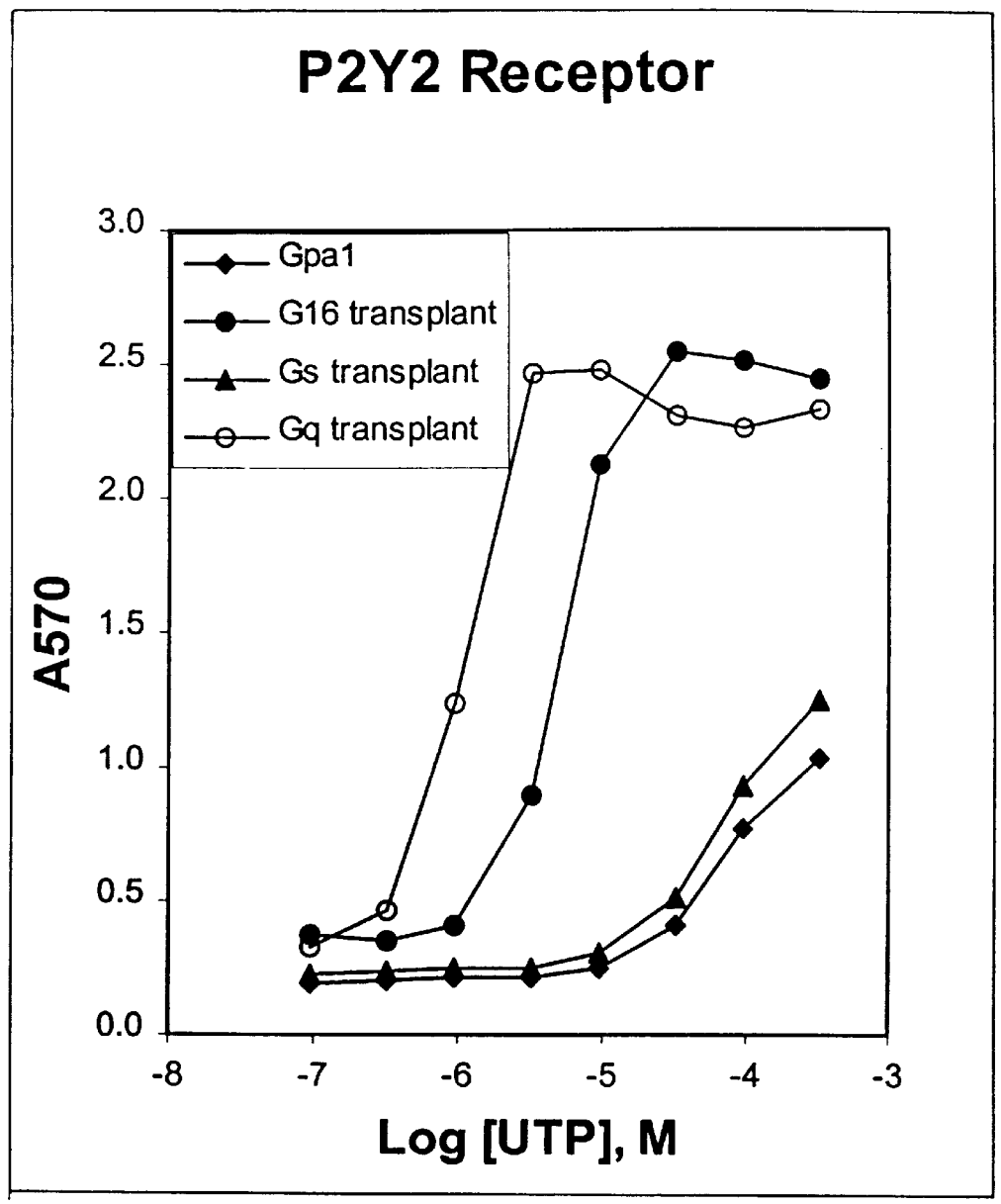

Fusions with longer N-terminal regions of Gpa1p and shorter regions of mammalian $G_\alpha$ subunits than the chimeras described above might still alter receptor specificity, given that minor modifications to the C-terminus of mammalian $G_\alpha$ subunits can change receptor specificity (7)(40)(23)(18). This could avoid the problem of chimeras having reduced affinity for $G_\beta/G_\delta$. We created a refined set of Gpa1-$G_\alpha$ fusions, designated the "transplants" (to distinguish them from the chimeras having longer regions of mammalian $G_\alpha$ (FIG. 5(B)). These fusions had the five C-terminal residues ($^{468}$KIGII$^{COOH}$) of Gpa1p replaced by the five C-terminal residues of $G_{\alpha 16}$ (EINLL$^{COOH}$), $G_{\alpha q}$ (EYNLV$^{COOH}$) or $G_{\alpha s}$ (QYELL$^{COOH}$) (see FIG. 5c. MMY9 cells were co-transformed with the transplant constructs, and in addition with pDT-PGK (vector with no heterologous receptor) or the receptor expression constructs pDT-PGK-5-HT$_{1A}$, pFL61-SST$_2$ or pDT-PGK-P2Y$_2$. As in Experiment 2, agonist-dependent activation of FUS1-LacZ was determined by incubating cells in medium supplemented with CPRG, and the extent of conversion to product after 24 hr incubation at 30° C. was determined by spectrophotometry. The results are depicted in FIGS. 4 A–D. This experiment shows that the transplants were able to interact efficiently with $G_\beta/G_\gamma$, since they reduced FUS1-LacZ expression in MMY9 cells to basal levels when expressed from the GPA1 promoter (FIG. 4a). In contrast to the C-terminal domain chimeras of Experiments 2 and 3, the Gpa1-$G_{\alpha 16}$, Gpa1-$G_{\alpha q}$ and Gpa1-$G_{\alpha s}$ transplants all retained the ability to couple the activated Ste2p receptor to the pheromone response pathway, although the dose-response curves suggested that compared to Gpa1p, the transplants interacted less efficiently with Ste2p (EC$_{50}$=257+/−13 nM; 75+/−2 nM; 102+/−5 nM; respectively for Gpa1-$G_{\alpha s}$, Gpa1-$G_{\alpha 16}$ and Gpa1-$G_{\alpha q}$)(FIG. 4a). With human receptors as opposed to the yeast receptor, the transplants improved $G_\alpha$ subunit/receptor interactions. The Gpa1-$G_{\alpha q}$ transplant significantly enhanced coupling of the P2Y$_2$ receptor relative to Gpa1p, consistent with the finding that P2Y$_2$ signals to its effector phospholipase Cβ via $G_{\alpha q}$ in mammalian cells. In contrast, the capacity of the Gpa1-$G_{\alpha s}$ transplant to couple P2Y$_2$ to the pheromone pathway was indistinguishable from that of Gpa1p.

The Gpa1-$G_{\alpha 16}$ transplant enhanced the agonist response of cells expressing three of the four human receptor (SST$_2$, 5-HT$_{1A}$, and P2Y$_2$ but not ML$_{1B}$). MMY9 cells coexpressing the Gpa1-$G_{\alpha 16}$ transplant with the SST$_2$ receptor required roughly ten-fold less somatostatin to elicit a similar response to control cells producing Gpa1p (EC$_{50}$=27+/−0.8 nM for Gpa1-$G_{\alpha 16}$; EC$_{50}$=430+/−44 nM for Gpa1p). The 5-HT$_{1A}$ receptor failed to signal in MMY9 cells through wild-type Gpa1p, but did so moderately well through the Gpa1-$G_{\alpha 16}$ transplant. For the SST$_2$ receptor, the Gpa1-$G_{\alpha 16}$ transplant was the most efficient $G_\alpha$; for the 5-HT$_{1A}$ and P2Y$_2$ receptors, the Gpa1-$G_{\alpha 16}$ transplant could support coupling but not as efficiently as the Gpa1/$G_{\alpha 0}$ chimera and the Gpa1-$G_{\alpha q}$ transplant, respectively.

Figure 7:
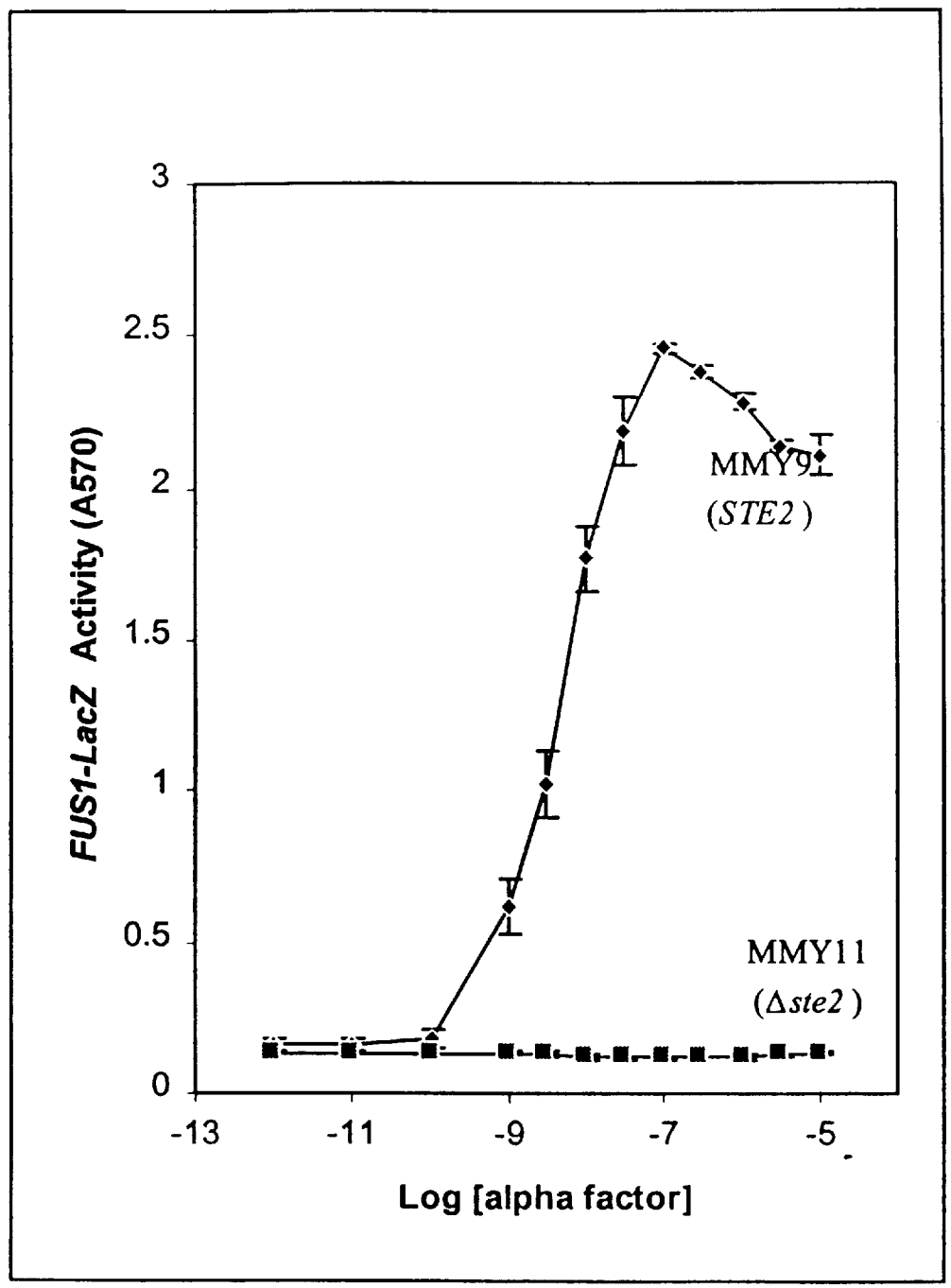
FIG. 7 shows the activity of the FUS1-lacZ reporter gene in MMY9 (STE2) and MMY11 (ΔSTE2) cells transformed with pRS314-Gpa1in response to incubation with the agonist, α-factor.

It has been reported (34) that deletion of the STE2 gene encoding the Ste2p α-factor receptor can result in enhanced coupling efficiencies of heterologously expressed receptors. This may be due to competition between the receptors for G-protein trimers. To investigate the effect of receptor competition on the function of receptors and $G_\alpha$ subunits described herein, we constructed a derivative of MMY9 in which the the STE2 gene was deleted by integrative disruption with the G418$^R$ resistance marker. The new strain was designated MMY11. This strain was used in an experiment in which MMY9 and MMY11 cells were transformed with the Gpa1p expression construct pRS314-GPA1 (FIG. 6c) and incubated with varying concentrations of α-factor in a CPRG assay (FIG. 7). As expected, MMY11 fails to respond to α-factor.

MMY11 was used in an experiment in which cells were transformed with pairs of plasmids as before, one to express a $G_\alpha$ subunit and the other a receptor expression construct. This experiment involved the four receptor expression constructs previously described herein (pFL61-SST$_2$, pDT-PGK-ML$_{1B}$, pDT-PGK-P2Y$_2$ and pDT-PGK-5-HT$_{1A}$) and four further receptor expression constructs: pDT-PGK-SST$_5$, pDT-PGK-A$_{2b}$, pDT-PGK-P2Y$_1$ and pDT-PGK-5-HT$_{1D}$. We constructed further transplant constructs to express modified versions of Gpa1p in which the C-terminal five amino acids were replaced with those of $G_{\alpha 0}$ (GCGLY$^{COOH}$), $G_{\alpha i1}$ (DCGLF$^{COOH}$), $G_{\alpha i3}$ (ECGLY$^{COOH}$), and $G_{\alpha 14}$ (EFNLV$^{COOH}$). These were used in this experiment, along with the $G_\alpha$ subunit expression constructs previously described herein. Cells were subjected to CPRG assays to determine the concentration response curve to agonist for each combination of receptor and $G_\alpha$ subunit. Where pheromone response pathway activation was detected, the agonist concentration required to yield a half-maximal response (EC50+/−standard error; all values in nM except where otherwise indicated) was determined by curve-fitting, and is shown in Table 4A. Where weak activation insufficient to carry out curve-fitting was detected, this is indicated in Table 4A (weak). Where no coupling was detected, this is also indicated (NC).

For comparison, Table 4B presents similar data obtained in MMY9; thus differences between the values in Tables 4A and 4B are likely to be due to the effect of Ste2p on signalling by heterologously expressed receptors.

TABLE 4A (MMY11):

| | | chimeras | | | | transplants | | | | | | |
|---|---|---|---|---|---|---|---|---|---|---|---|---|
| | Gpa1p | Gpa1/$G_{\alpha o}$ | Gpa1/$G_{\alpha i1}$ | Gpa1/$G_{\alpha i2}$ | Gpa1/$G_{\alpha i3}$ | Gpa1/$G_{\alpha q}$ | Gpa1/$G_{\alpha o}$ | Gpa1/$G_{\alpha i1}$ | Gpa1/$G_{\alpha i3}$ | Gpa1/$G_{\alpha s}$ | Gpa1/$G_{\alpha 14}$ | Gpa1/$G_{\alpha 16}$ |
| $SST_2$ | 69 ± 2 | 46 ± 2 | 91 ± 6 | 30 ± 2 | 47 ± 1 | weak | 65 ± 4 | 5.6 ± 0.6 | 1.8 ± 0.1 | NC | 49 ± 0.5 | 7.0 ± 0.6 |
| $SST_5$ | 26 ± 0.8 | 115 ± 4 | 137 ± 8 | 56 ± 3 | 97 ± 4 | 66 ± 3 | 11 ± 0.5 | 4.9 ± 0.2 | 3.6 ± 0.2 | weak | 19 ± 0.5 | 3.8 ± 0.1 |
| 5-$HT_{1A}$ | weak | 390 ± 14 $\mu M$ | 11 ± 0.5 $\mu M$ | 2.5 ± 0.2 $\mu M$ | 7 ± 0.5 $\mu M$ | weak | 1.0 ± 0.1 $\mu M$ | 1.3 ± 0.1 $\mu M$ | 1.1 ± 0.05 $\mu M$ | weak | 1.7 ± 0.1 $\mu M$ | 1.7 ± 0.1 $\mu M$ |
| 5-$HT_{1D}$ | NC | 2.0 ± 1.1 $\mu M$ | 3.4 ± 1.6 $\mu M$ | 355 ± 82 | 1.8 ± 0.5 $\mu M$ | NC | weak | 227 ± 20 | 135 ± 12 | NC | NC | weak |
| $ML_{1B}$ | 912 ± 300 | weak | weak | 407 ± 200 | NC | NC | 500 ± 200 | 14 ± 5 | 26 ± 5 | NC | NC | 1.4 ± 0.15 $\mu M$ |
| $P2Y_1$ | NC | NC | NC | NC | NC | 27 ± 14 $\mu M$ | NC | weak | weak | NC | 12 ± 2.5 $\mu M$ | NC |
| $P2Y_2$ | weak | NC | NC | NC | NC | 3.8 ± 0.1 $\mu M$ | 18 ± 2 $\mu M$ | 5.2 ± 0.5 $\mu M$ | 2.0 ± 0.2 $\mu M$ | weak | 3.3 ± 0.08 $\mu M$ | 4.64 ± 0.06 $\mu M$ |
| $A2_B$ | 43 ± 2 | NC | NC | NC | NC | 197 ± 8 | 51 ± 2.5 | 16 ± 0.8 | 87 ± 8 | 30 ± 2.3 | 58 ± 1.9 | 40 ± 3 |

Values in nM except where otherwise indicated.

TABLE 4B (MMY9):

| | | chimeras | | | | transplants | | | | | | |
|---|---|---|---|---|---|---|---|---|---|---|---|---|
| | Gpa1p | Gpa1/$G_{\alpha o}$ | Gpa1/$G_{\alpha i1}$ | Gpa1/$G_{\alpha i2}$ | Gpa1/$G_{\alpha i3}$ | Gpa1/$G_{\alpha q}$ | Gpa1/$G_{\alpha o}$ | Gpa1/$G_{\alpha i1}$ | Gpa1/$G_{\alpha i3}$ | Gpa1/$G_{\alpha s}$ | Gpa1/$G_{\alpha 14}$ | Gpa1/$G_{\alpha 16}$ |
| Ste2p | 5.2 ± 0.4 | 2 ± 0.1 $\mu M$ | weak | 21 ± 2 $\mu M$ | NC | 102 ± 5 | 31 ± 4 | 87 ± 1.5 | 14 ± 2 | 257 ± 13 | 288 ± 50 | 75 ± 2 |
| $SST_2$ | 430 ± 44 | 300 ± 38 | 650 ± 65 | 300 ± 22 | 630 ± 30 | weak | ND | ND | ND | NC | ND | 27 ± 0.8 |
| 5-$HT_{1A}$ | NC | 2.6 ± 0.4 $\mu M$ | weak | weak | weak | weak | ND | ND | ND | weak | ND | weak |
| $ML_{1B}$ | 5.3 ± 0.3 $\mu M$ | weak | weak | 1.4 ± 0.2 $\mu M$ | NC | NC | ND | ND | ND | NC | ND | weak |
| $P2Y_2$ | weak | NC | NC | NC | NC | 3.6 ± 0.4 $\mu M$ | ND | ND | ND | weak | ND | 16 ± 0.6 $\mu M$ |

Values in nM except where otherwise indicated.
ND indicates not determined.

This experiment further illustrates that coupling efficiencies can be substantially enhanced by this "transplant" type of modification, even compared to the chimeric Gpa1/$G_\alpha$ subunits described in Experiments 2 and 3. Coupling of me Ste2p receptor was supported by all of the transplants, although none were as effective as wild-type Gpa1p, as indicated by the greater concentrations of α-factor required to elicit half-maximal responses (Table 4B). However, the transplants in general enhanced the coupling of human receptors, relative to wild-type Gpa1p (Table 4A) as indicated by me lower concentrations of agonists required to elicit half-maximal responses. All of the transplants enhanced $P2Y_2$ signalling except Gpa1-$G_{\alpha s}$, which was not significantly different from wild-type Gpa1p. Most efficient was the Gpa1-$G_{\alpha i3}$ transplant. Similarly, the transplants enhanced the efficiency of coupling of the $SST_2$, $SST_5$, $ML_{1B}$, 5$HT_{1D}$ and $A_{2b}$ receptors, relative to either Gpa1p or to the chimeras with long C-terminal domains of $G_{\alpha i/o}$, often with ten-fold or greater reductions in $EC_{50}$. The $P2Y_1$ receptor could be coupled to the pheromone response pathway only by transplants, with the Gpa1-$G_{\alpha 14}$ transplant being most efficient. It is Informative to compare the Gpa1/$G_{\alpha i2}$ chimera and Gpa1-$G_{\alpha i1}$ transplant, which differ only in the length of sequence derived from the mammalian $B^\alpha$(as the C-terminal five amino acids of $G^{\alpha i1}$ and $G_{\alpha i2}$ are identical). The $EC_{50}$ values for $ML_{1B}$ and $SST_2$ were more than ten-fold lower with the Gpa1-$G_{\alpha i1}$ transplant than with the Gpa1/$G_{\alpha i2}$ chimera. The same comparison can be made for the Gpa1/$G_{\alpha i3}$ chimera and Gpa1-$G_{\alpha i3}$ transplant. Clearly, chimeras With shorter lengths of mammalian $G_\alpha$ subunits can give more efficient coupling of some receptors. The only receptor In this study for which a transplant did not yield optimal coupling efficiency was 5$HT_{1A}$ where the most efficient transplant was Gpa1-$G_{\alpha o}$($EC_{50}$ in MMY11; 1.0±0.1 $\mu M$) but the most efficient coupling was achieved with the Gpa1/$G_{\alpha o}$ chimera ($EC_{50}$ in MMY11; 390±14 nM). This suggests that for the majority of mammalian receptors, most efficient coupling in yeast will be achieved with the transplant type of $G_\alpha$ subunit.

Comparison of $EC_{50}$ values obtained in MMY9 and MMY11 for identical combinations of receptor and $G_\alpha$ subunit indicates that the absence of Ste2p can enhance coupling efficiencies by approximately 10-fold. Moreover, for certain poorly compatible receptor/G-protein combinations coupling could be detected in MMY11 but not in MMY9, for example 5$HT_{1A}$ and Gpa1p. This is fully consistent with the previously observed effects of deleting the STE2 gene, reported by Price et al. (34), and does not affect the conclusions above.

We created a further construct to express a truncated Gpa1p molecule lacking the five C-terminal amino acids (FIG. 8D). This truncation mutant has been reported to bind $G_\beta/G_\gamma$ but fail to couple Ste2p to the pheromone response pathway (11). As expected, expression of this truncated Gpa1p mutant in MMY9 or MMY11 cells resulted in low levels of FUS1-LacZ activity, indicating the truncated mutant can bind $G_\beta/G_\gamma$ (data not shown). In the CPRG β-galactosidase assay, this mutant fails to couple either Ste2p or other receptors to the pheromone response pathway (data not shown). This is fully consistent with the report of Hirsch et al. (11) and confirms the importance of the five C-terminal amino acids of the $G_\alpha$ subunit in the interaction with G-protein coupled receptors.

Figure 8A:
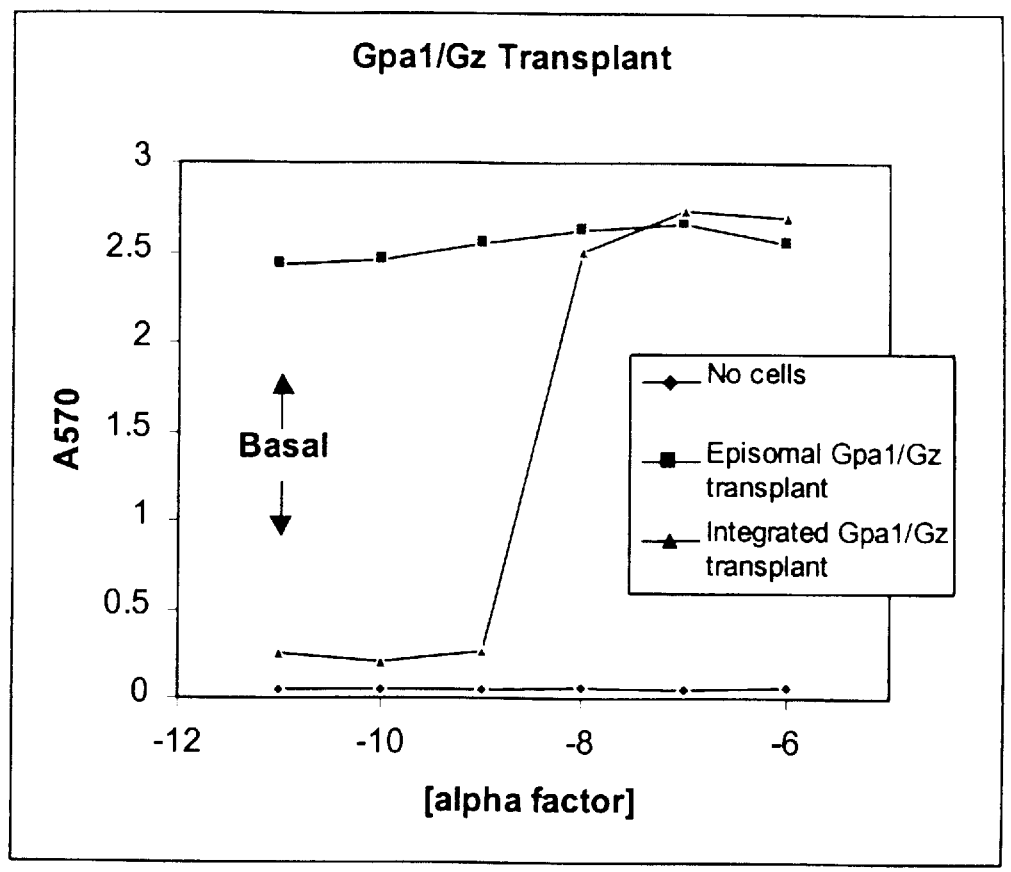
FIGS. 8a–c show comparisons of isogenic yeast strains containing either episomal or integrated constructs expressing the transplants Gpa1-$G_{\alpha z}$ (FIG. 8a), Gpa1-$G_{\alpha 13}$ (FIG. 8b), and Gpa1-$G_{\alpha 12}$ (FIG. 8c). Cells were deleted for the endogenous STE2 gene but were transformed with a plasmid (Yep24-STE2) to express Ste2p to enable detection of FUS1-lacZ reporter gene activation in response to α-factor.
Figure 8B:
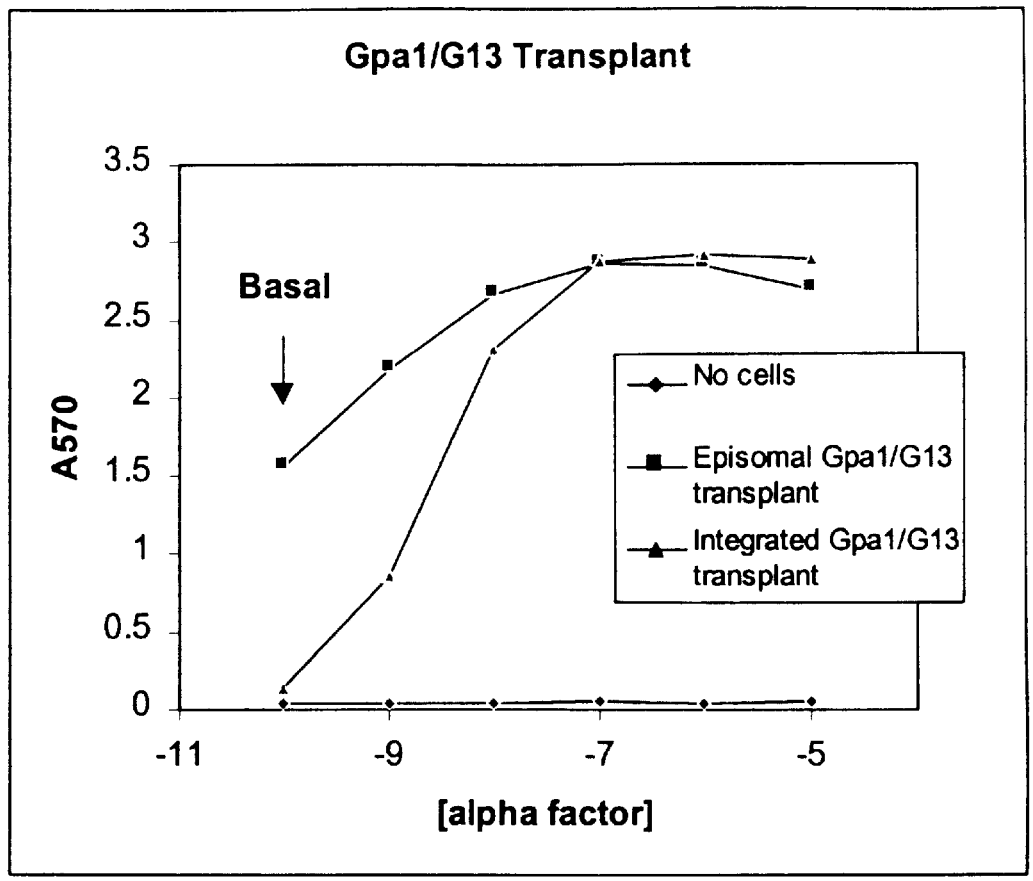
Figure 8C:
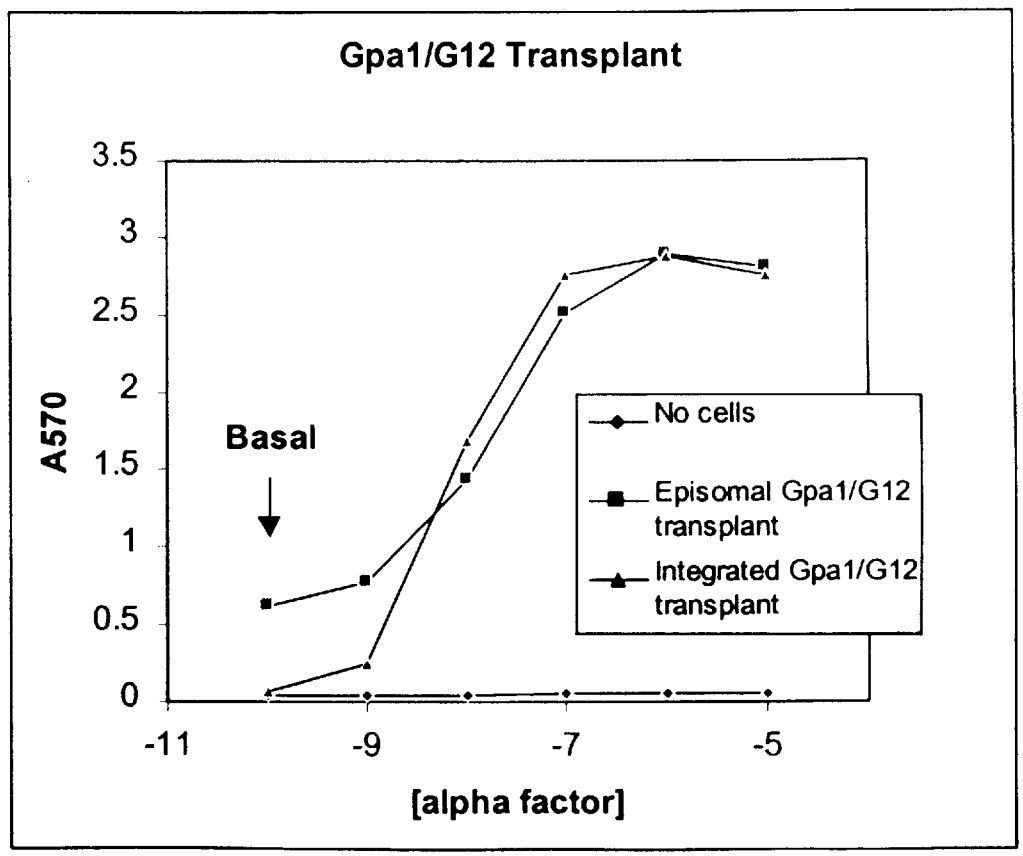

We made further transplant constructs to express modified versions of Gpa1p in which the C-terminal five amino acids were replaced with those of $G_{\alpha z}$ (YIGLC$^{COOH}$), $G_{\alpha 12}$ (DIMLQ$^{COOH}$) and $G_{\alpha 13}$ (QLMLQ$^{COOH}$). The Gpa1-$G_{\alpha z}$, Gpa1-$G_{\alpha 13}$ and to a lesser extent the Gpa1-$G_{\alpha 12}$ transplants expressed from the pRS314-Gpa1-$G_{\alpha z}$, pRS314-Gpa1-$G_{\alpha 13}$, and pRS314-Gpa1-$G_{\alpha 12}$ constructs were all able to couple the Ste2p receptor but they failed to fully sequester $G_\beta/G_\gamma$ as they were associated with increased basal levels of FUS1-LacZ activity even in the absence of receptor activation (FIG. 8). Conceivably, this might be due to disrupted interaction with $G_\beta/G_\gamma$, or to activation by an endogenous yeast protein, or reduced plasmid stability (see below). Quantitative immunoblotting suggested that all transplant proteins were produced to similar levels. We created further plasmids in which the Gpa1-$G_{\alpha z}$, Gpa1-$G_{\alpha 13}$ and Gpa1-$G_{\alpha 12}$ expression cassettes were contained in pRS304. The plasmid pRS304 is an integrating vector whereas pRS314 is an episomal, centromeric vector. The pRS304-Gpa1-$G_{\alpha z}$, pRS304-Gpa1-$G_{\alpha 13}$, and pRS304-Gpa1-$G_{\alpha 12}$ constructs were transformed into MMY11, targetting their integration into the trp1 locus of this strain. The resultant strains expressed the Gpa1-$G_{\alpha z}$, Gpa1-$G_{\alpha 13}$ and Gpa1-$G_{\alpha 12}$ transplants from genes located chromosomally rather than from genes located on free, episomal plasmids. In the experiment presented in FIG. 8, MMY11 cells were transformed with either pRS304-based or pRS314-based (integrating and episomal, respectively) plasmids to express Gpa1-$G_{\alpha z}$ (FIG. 8a), Gpa1-$G_{\alpha 13}$ (FIG. 8b), or Gpa1-$G_{\alpha 12}$ (FIG. 8c) transplants. In addition, cells were transformed with Yep24-STE2 to express the STE2 gene, as this had been deleted from the MMY11 strain. Activation of FUS1-LacZ in response to different concentrations of α-factor was determined in a CPRG assay. This experiment shows that integrating the transplant expression constructs into the chromosome reduces basal levels of FUS1-LacZ activity in the absence of receptor activation. This enables the Gpa1-$G_{\alpha z}$, Gpa1-$G_{\alpha 13}$ and Gpa1-$G_{\alpha 12}$ transplants to be tested in experiments with the human receptor expression constructs for their ability to couple heterologously expressed receptors (data not shown).

We carried out the same approach, of transferring the transplant expression cassette to a pRS304 plasmid and integrating into the genome of MMY11, for other transplants. This created a series of strains expressing chromosomal copies of the Gpa1-$G_{\alpha O}$, Gpa1-$G_{\alpha i1}$, Gpa1-$G_{\alpha i3}$, Gpa1-$G_{\alpha 14}$, Gpa1-$G_{\alpha S}$-$G_{\alpha q}$, Gpa1-Gpa$_{16}$ Gpa1-$G_{\alpha z}$, Gpa1-$G_{\alpha 13}$ and Gpa1-$G_{\alpha 12}$ transplants. In all cases, we observed the phenomenon described above, of reduced basal levels of FUS1-LacZ activity in the absence of receptor activation, without affecting EC50. We conclude from this result that the episomal $G_\alpha$ subunits constructs are unstable. We postulate that in a population of cells containing an episomal $G_\alpha$ plasmid, a small proportion of cells may lose this plasmid. These cells would not be propagated as they lack the URA3 gene. However, because they would lack any $G_\alpha$ subunit the pheromone response pathway would be constitutively activated and they would accumulate the LacZ enzyme. Thus elevated basal FUS1-lacZ levels would be apparent in the whole population, without changing apparent protein levels. With the integrated copy of the gene encoding $G_\alpha$, this does not occur.

The set of strains containing the full range of integrated transplants represents the full diversity of known mammalian $G_\alpha$ subunits likely to be relevant to drug discovery ($G_{\alpha t}$ and $G_{\alpha olf}$ transplants have not been tested). The same approach of constructing transplants may be taken with any $G_\alpha$ subunits discovered in the future.

In conclusion, this approach represents a significant improvement over previously described technologies, because i) it is applicable to a wider range of $G_\alpha$ subunits, ii) it is applicable to $G_{\alpha 16}$ in particular and iii) the Gpa1-$G_{\alpha 16}$ transplant possesses, at least to some degree, the property of $G_{\alpha 16}$ of interacting with a broad range of receptors, and therefore may be the $G_\alpha$ subunit of choice for coupling orphan receptors, for which the physiologically relevant G protein targets are unknown.

BIBLIOGRAPHY

1. Baldwin, J. M. 1994. Current Opinion in Cell Biology 6:180–190.
2. Bertin, B., et.al. 1992. Journal of Biological Chemistry 267:8200–8206.
3. Blumer, K. J. and J. Thorner. 1990. Proc. Natl. Acad. Sci. U. S. A. 87:4363–4367.
4. Bourne, H. R. 1997. Current Opinion in Cell Biology 9:134–142.
5. Butkerait, P., et.al. 1995. Journal of Biological Chemistry 270:18691–18699.
6. Cerione, R. A., et.al. 1988. J. Biol. Chem. 263:9345–9352.
7. Conklin, B. R., et.al. 1993. Nature 363:274–276.
8. Fargin, A., et.al. 1991. Cellular Signalling 3:547–557.
9. Hamm, H. E., et.al. 1988. Science 241:832–835.
10. Hamm, H. E., et.al. 1987. J. Biol. Chem. 262:10831–10838.
11. Hirsch, J. P., et.al. 1991. Genes & Development 5:467–474.
12. Kajkowski, E. M., et.al. 1997. Journal of Receptor & Signal Transduction Research 17:293–303.
13. Kallal, L. and J. Kurjan. 1997. Molecular & Cellular Biology 17:2897–2907.
14. Kang, Y. S., et.al. 1990. Molecular & Cellular Biology 10:2582–2590.
15. Kleuss, C., et.al. 1993. Science 259:832–834.
16. Kleuss, C., et.al. 1992. Science 358:424–426.
17. Koelle, M. R. 1997. Current Opinion in Cell Biology 9:143–147.
18. Komatsuzaki, K., et.al. 1997. FEBS Letters 406:165–170.
19. Lambright, D. G., et.al. 1996. Nature 379:311–319.
20. Leberer, E., et.al. 1997. Current Opinion in Genetics & Development 7:59–66.
21. Lee, C. H., et.al. 1995. Molecular Pharmacology 47:218–223.
22. Lichtarge, O., et.al. 1996. Proc. Natl. Acad. Sci. U. S. A. 93:7507–7511.
23. Liu, J., et.al. 1995. Proc. Natl. Acad. Sci. U. S. A. 92:11642–11646.
24. Maniatis, T., et.al.. 1982. Molecular Cloning, A Laboratory Manual. Cold Spring Harbor Laboratory Press, Cold Spring Harbor, N.Y.
25. Miller, J. H. 1972. Experiments in Molecular Genetics. Cold Spring Harbor Laboratory Press, Cold Spring Harbor, N.Y.
26. Milligan, G., et.al. 1996. Trends in Pharmacological Sciences 17:235–237.

27. Minet, M., et.al. 1992. Plant Journal 2:417–422.
28. Oliner, J. D., et.al. 1993. Nucleic. Acids. Res. 21:5192–5197.
29. Onrust, R., et.al. 1997. Science 275:381–384.
30. Palm, D., et.al. 1990. FEBS Lett. 261:294–298.
31. Parr, C. E., et.al. 1994.. Proc. Natl. Acad. Sci 91:3275–3279.
32. Parr, C. E., et.al. 1994. Proc. Natl. Acad. Sci. 91:13067.
33. Price, L. A., et.al. 1995. Molecular & Cellular Biology 15:6188–6195.
34. Price, L. A., et.al. 1996. Molecular Pharmacology 50:829–837.
35. Rasenick, M. M., et.al. 1994. J. Biol. Chem. 269:21519–21525.
36. Simonds, W. F., et.al.. 1989. Proc. Natl. Acad. Sci. U. S. A. 86:7809–7813.
37. Slater, M. R. and E. A. Craig. 1987. Molecular & Cellular Biology 7:1906–1916.
38. Tesmer, J. J., et.al. 1997. Cell 89:251–261.
39. Van Dop, C., G. et.al. 1984. J. Biol. Chem. 259:23–26.
40. Voyno-Yasenetskaya, T., et.al. 1994. J. Biol. Chem. 269:4721–4724.
41. Wall, M. A., et.al. 1995. Cell 83:1047–1058.

What is claimed is:

1. A chimeric $G_\alpha$ protein having a yeast $G_\alpha$ (Gpa1p) amino acid sequence wherein 5 consecutive amino acid positions within the C-terminal 10 amino acids of Gpa1p are substituted with the corresponding 5 consecutive amino acids from the C-terminal 10 amino acids of a mammalian $G_\alpha$ protein.

2. A chimeric $G_\alpha$, protein comprising the N-terminal 467 amino acids of yeast $G_\alpha$ (Gpa1p) protein and the C-terminal 5 amino acids from a mammalian $G_\alpha$ protein.

3. A chimeric $G_\alpha$ protein having the N-terminal 467 amino acids of yeast $G_\alpha$ (Gpa1p) protein and the C-terminal 5 amino acids from a $G_\alpha$ protein selected from: $G_{\alpha q}$, $G_{\alpha s}$, $G_{\alpha 0}$, $G_{\alpha i1}$, $G_{\alpha i3}$, $G_{\alpha z}$, $G_{\alpha 12}$, $G_{\alpha 13}$, $G_{\alpha 14}$, and $G_{\alpha 16}$.

4. A nucleic acid molecule encoding a chimeric $G_\alpha$ protein according to any one of claims 1 to 3.

5. A transformed yeast cell comprising a nucleic acid molecule which encodes a heterologous G protein-coupled receptor and a nucleic acid molecule according to claim 4.

6. A method of screening for a compound which interacts with a mammalian receptor comprising contacting a compound of interest with a cell according to claim 5 with a test compound and observing the growth response of the call compared to the growth response that would occur in the absence of said test compound.

7. A method according to claim 6 wherein the cell further comprises a reporter gene and the method includes the step of observing the production of a reporter gene product.

* * * * *